United States Patent
Kutose et al.

(10) Patent No.: US 8,222,430 B2
(45) Date of Patent: Jul. 17, 2012

(54) 1-HETERODIENE DERIVATIVE AND HARMFUL ORGANISM CONTROL AGENT

(75) Inventors: Koichi Kutose, Takaoka (JP); Jyun Takahashi, Odawara (JP); Isami Hamamoto, Odawara (JP); Makio Yano, Nagareyama (JP); Jyunko Morohoshi, Ryugasaki (JP); Jyun Kanazawa, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 13/139,859

(22) PCT Filed: Dec. 17, 2009

(86) PCT No.: PCT/JP2009/006962
§ 371 (c)(1),
(2), (4) Date: Jun. 15, 2011

(87) PCT Pub. No.: WO2010/070910
PCT Pub. Date: Jun. 24, 2010

(65) Prior Publication Data
US 2011/0251388 A1  Oct. 13, 2011

(30) Foreign Application Priority Data
Dec. 19, 2008  (JP) ............................... 2008-324515

(51) Int. Cl.
C07D 335/02 (2006.01)
C07D 211/40 (2006.01)
C07D 207/12 (2006.01)
C07D 405/12 (2006.01)
C07D 333/36 (2006.01)
C07D 313/04 (2006.01)
C07D 309/14 (2006.01)
C07D 307/22 (2006.01)

(52) U.S. Cl. .............. 549/28; 546/242; 548/541; 549/9; 549/68; 549/346; 549/424; 549/480

(58) Field of Classification Search ............... 549/9, 28, 549/68
See application file for complete search history.

(56) References Cited

U.S. PATENT DOCUMENTS
4,476,307 A  10/1984  Howard, Jr. et al.
4,950,666 A  8/1990  Peake et al.

FOREIGN PATENT DOCUMENTS
DE  199 61 465  7/2000
JP  11-500114  1/1999
JP  11-199410  7/1999
JP  2002-509917  4/2002
WO  98/13361  4/1998
WO  2008/152091  12/2008

OTHER PUBLICATIONS

Danishefsky, Total Synthesis of Pretyrosine (Arogenate), 1981, J. Am. Chem. Soc. vol. 103, p. 1602-1604.*
Tojino, Cyclizative radical carbonylations of azaenynes by TTMSS and hexanethiol leading to alpha-silyl- and thiomethylene lacams. Insights into the E/Z steroselectivites, 2003, Org. Biomol. Chem. vol. 1, p. 4262-4267.*
Sakamoto, Masami, et al., "Photochemical Isomerization of O-Allyl and O-But-3-enyl Thiocarbamates", J. Chem. Soc. Perkin Trans 1, 1995, pp. 373-377.
Xiong Tao, et al., "A Divergent Synthesis of γ-Iminolactones, Dihydroquinolin-2-ones, and γ-Lactames from β-Hydroxymethylcyclopropanylamides", J. Org. Chem., 2007, vol. 72, pp. 8005-8009.
Meyer, Walter L., et al., "1,5-Diaryl-2,3-pyrrolidinediones. VIII. Synthesis and Structure Proof", Journal of Organic Chemistry, 1957, vol. 22, pp. 1554-1560.
Padwa, Albert, et al., "Additive and Vinylogous Pummerer Reactions of Amido Sulfoxides and Their Use in the Preparation of Nitrogen Containing Heterocycles", J. Org. Chem., 1998, vol. 63, pp. 4256-4268.
International Search Report issued for PCT/JP2009/006962, mailed on Mar. 16, 2010, 5 pages.
European Search Report issued for EP Application No. 09833217.4, mailed on May 16, 2012, 7 pages.

* cited by examiner

*Primary Examiner* — Golam M M Shameem
*Assistant Examiner* — Karen Cheng
(74) *Attorney, Agent, or Firm* — Kenyon & Kenyon LLP

(57) ABSTRACT

The present invention provides a 1-heterodiene derivative represented by formula (2) or salt thereof: (in formula (2), W represents hydrogen atom or the like, A represents oxygen atom or the like, $R^1$ represents an optionally substituted C1-6 alkyl group or the like, m represents an integer of 0 to 10, n represents an integer of 1 to 4, $X^1$ represents oxygen atom or the like, p represents an integer of 0 to 5, $R^3$ represents an optionally substituted C1-6 alkyl group or the like, r presents an integer of 0 to 5, the 1-heterodiene derivative exists in E-form, Z-form or a mixture thereof according to the carbon-carbon undefined double stereo bond in formula (2)).

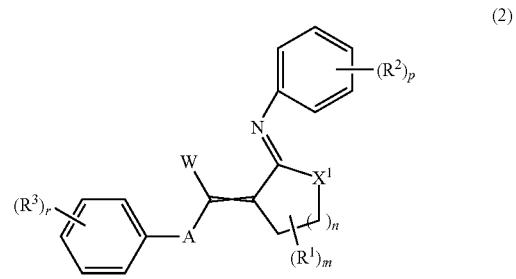

(2)

2 Claims, No Drawings

1-HETERODIENE DERIVATIVE AND HARMFUL ORGANISM CONTROL AGENT

TECHNICAL FIELD

The present invention relates to a new 1-heterodiene derivative or salt thereof, and relates to a harmful organism control agent containing the 1-heterodiene derivative or salt thereof as an active ingredient.

Priority is claimed on Japanese Patent Application No. 2008-324515, filed Dec. 19, 2008, the content of which is incorporated herein by reference.

BACKGROUND ART

Until now, numerous compounds having insecticidal activity and miticidal activity have been known. However, there have been problems in that that their efficacy is insufficient, in that their use is limited due to drug resistance problems, or in that they have caused harmful effects or contamination in plants, or they are strongly toxic with respect to humans, animals, fish, and the like.

As a compound having similar skeleton to the compound of the present invention, a compound represented by formula (3) is described in non-patent document 1, and a compound represented by formula (4) is described in non-patent document 2. However, the physiological activities of these compounds described in the non-patent documents are unknown.

Moreover, a compound represented by formula (5) is described in patent document 1. However, the patent document merely shows that this compound is medicinally applicable.

[Chemical formula 1]

(3)

[Chemical formula 2]

(4)

[Chemical formula 3]

(5)

PRIOR ART LITERATURE

Patent Document

Patent document 1: U.S. Pat. No. 4,476,307

Non-Patent Document

Non-patent document 1: J. Chem. Soc., Perkin Trans 1, 1995, 373-378

Non-patent document 2: J. Org. Chem., 72, 8005-8009 (2007)

DISCLOSURE OF INVENTION

Problems to be Solved by the Invention

The objective of the present invention is to provide a harmful organism control agent having a new skeleton, which can be industrially and expediently synthesized and has an excellent biological activity and residual efficacy.

Means for Solving the Problems

As a result of conducting extensive studies to achieve the above objective, the inventors of the present invention discovered that a 1-heterodiene derivative having a specific structure has an excellent insecticidal activity and miticidal activity.

Namely, the present invention is as follows:
(1) A 1-heterodiene derivative represented by formula (1) or salt thereof:

[Chemical formula 4]

(1)

In formula (1), $Q^1$ represents an optionally substituted C2-6 alkenyl group, an optionally substituted C2-6 alkynyl group, an optionally substituted C3-6 cycloalkyl group, an optionally substituted C4-8 cycloalkenyl group, an optionally substituted C6-10 aryl group, an optionally substituted benzyl group or an optionally substituted heterocyclic group, W represents hydrogen atom or an optionally substituted C1-6 alkyl group, X represents oxygen atom, sulfur atom or N-$Q^2$ ($Q^2$ represents an optionally substituted C2-6 alkenyl group, an optionally substituted C2-6 alkynyl group, an optionally substituted C3-6 cycloalkyl group, an optionally substituted C4-8 cycloalkenyl group, an optionally substituted C6-10 aryl group, an optionally substituted benzyl group, an optionally substituted C6-10 aryloxy group, an optionally substituted C6-10 arylamino group or an optionally substituted heterocyclic group), Y represents oxygen atom, sulfur atom or N-$Q^3$ ($Q^3$ represents an optionally substituted C2-6 alkenyl group, an optionally substituted C2-6 alkynyl group, an optionally substituted C3-6 cycloalkyl group, an optionally substituted C4-8 cycloalkenyl group, an optionally substituted C6-10 aryl group, an optionally substituted benzyl group, an optionally substituted C6-10 aryloxy group, an optionally substituted C6-10 arylamino group or an optionally substituted heterocyclic group), provided that when X represents oxygen atom or sulfur atom, Y represents N-$Q^3$, when X represents N-$Q^2$, Y represents oxygen atom or sulfur atom, A represents oxygen atom, sulfur atom, sulfonyl group or sulfonyl group, n represents an integer of 1 to 4, $R^1$ represents an optionally substituted C1-6 alkyl group, an optionally substituted C2-6 alkenyl group, an optionally substituted C2-6 alkynyl group, an optionally substituted C3-6 cycloalkyl group, an optionally substituted C4-8 cycloalkenyl group, an optionally substituted C6-10 aryl group, an optionally substituted heterocyclic group, an optionally substituted C1-11 acyl group, an optionally substituted (1-imino) C1-6 alkyl group, an optionally substituted hydroxy group, an optionally substituted amino group, an optionally substituted mercapto group, a substituted sulfonyl group, a substituted sulfinyl group, a silyl group, a halogen group, cyano group or nitro group, m represents an integer of 0 to 10, when m is 2 or more, $R^1$ may be the same or different from each other, more than one $R^1$ may bond together to form an optionally substituted 3- to 8-membered ring, the 1-heterodiene derivative exists in E-form, Z-form or a mixture thereof according to the carbon-carbon undefined double stereo bond in formula (1).

(2) A 1-heterodiene derivative represented by formula (2) or salt thereof:

[Chemical formula 5]

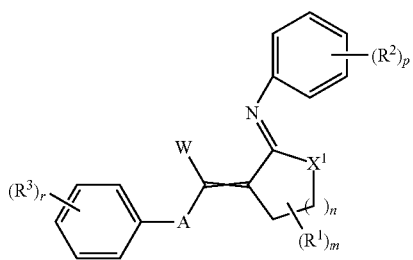

(2)

In formula (2), W, A, $R^1$, m and n are as defined above, $X^1$ represents oxygen atom or sulfur atom, $R^2$ represent an optionally substituted C1-6 alkyl group, an optionally substituted C2-6 alkenyl group, an optionally substituted C2-6 alkynyl group, an optionally substituted C3-6 cycloalkyl group, an optionally substituted C4-8 cycloalkenyl group, an optionally substituted C6-10 aryl group, an optionally substituted heterocyclic group, an optionally substituted C1-11 acyl group, an optionally substituted (1-imino) C1-6 alkyl group, an optionally substituted hydroxy group, an optionally substituted amino group, an optionally substituted mercapto group, a substituted sulfonyl group, a substituted sulfinyl group, a silyl group, a halogen group, cyano group or nitro group, p represents an integer of 0 to 5, when p is 2 or more, $R^2$ may be the same or different from each other, more than one $R^2$ may bond together to form an optionally substituted 3- to 8-membered ring, $R^3$ represents an optionally substituted C1-6 alkyl group, an optionally substituted C2-6 alkenyl group, an optionally substituted C2-6 alkynyl group, an optionally substituted C3-6 cycloalkyl group, an optionally substituted C4-8 cycloalkenyl group, an optionally substituted C6-10 aryl group, an optionally substituted heterocyclic group, an optionally substituted C1-11 acyl group, an optionally substituted (1-imino) C1-6 alkyl group, an optionally substituted hydroxy group, an optionally substituted amino group, an optionally substituted mercapto group, a substituted sulfonyl group, a substituted sulfinyl group, a silyl group, a halogen group, cyano group or nitro group, r represents an integer of 0 to 5, when r is 2 or more, $R^3$ may be the same or different from each other, more than one $R^3$ may bond together to form an optionally substituted 3- to 8-membered ring, the 1-heterodiene derivative exists in E-form, Z-form or a mixture thereof according to the carbon-carbon undefined double stereo bond of formula (2).

(3) A harmful organism control agent containing, as an active ingredient, the 1-heterodien derivative or salt thereof according to the above-described (1) or (2).

Effects of the Invention

According to the present invention, a 1-heterodiene derivative having a new structure and salt thereof can be provided. In addition, a harmful organism control agent containing, as an active ingredient, the 1-heterodiene derivative or salt thereof can be provided. The harmful organism control agent has an excellent biological activity, especially a biological activity against insects or mites, and has a high safety.

BEST MODE FOR CARRYING OUT THE INVENTION

Hereafter, the 1-heterodiene derivative of the present invention will be described in detail based on formula (1) and (2). In addition, in this description, "Ca-b xxx group" and "Cc xxx group" indicate that the groups have a carbon number of a to b, or a carbon number of c.

The "unsubstituted C2-6 alkenyl group" indicates a linear or branched C2-6 alkenyl group having a carbon-carbon double bond in one or more alkyl moieties. For example, vinyl group, 1-propenyl group, allyl group, 1-butenyl group, 2-butenyl group, 3-butenyl group, 1-pentenyl group, 2-pentenyl group, 3-pentenyl group, 4-pentenyl group, 1-hexenyl group, 2-hexenyl group, 3-hexenyl group, 4-hexenyl group, 5-hexenyl group, 1-methyl-2-propenyl group, 2-methyl-2-propenyl group, 1-methyl-2-butenyl group, 2-methyl-2-butenyl group or the like may be cited. Among these, a C2-4 alkenyl group is preferable.

The "unsubstituted C2-6 alkynyl group" indicates a linear or branched C2-6 alkynyl group having a carbon-carbon triple bond in one or more alkyl moieties. For example, ethynyl group, 1-propynyl group, propargyl group, 1-butynyl group, 2-butynyl group, 3-butynyl group, 1-pentynyl group, 2-pentynyl group, 3-pentynyl group, 4-pentynyl group, 1-hexynyl group, 1-methyl-2-propynyl group, 2-methyl-3-butyryl group, 1-methyl-2-butynyl group, 2-methyl-3-pentynyl group, 1,1-dimethyl-2-butynyl group or the like may be cited. Among these, a C2-4 alkynyl group is preferable.

The "unsubstituted C3-6 cycloalkyl group" indicates a C3-6 alkyl group having a cyclic moiety. For example, cyclopropyl group, cyclobutyl group, cyclopentyl group, cyclohexyl group or the like may be cited.

The "unsubstituted C4-8 cycloalkenyl group" indicates a C4-8 alkenyl group having a cyclic moiety. For example, 1-cyclobutenyl group, 1-cyclopentenyl group, 3-cyclopentenyl group, 1-cyclohexenyl group, 3-cyclohexenyl group, 3-cycloheptenyl group, 4-cyclooctenyl group or the like may be cited.

The "unsubstituted C6-10 aryl group" indicates a monocyclic or polycyclic C6-10 aryl group. In the polycyclic aryl group, if there exists at least one aromatic ring, the other rings may be saturated aliphatic rings, unsaturated aliphatic rings or aromatic rings. For example, phenyl group, naphthyl group, azulenyl group, indenyl group, indanyl group, tetralinyl group or the like may be cited. Among these, phenyl group is preferable.

The "unsubstituted heterocyclic group" indicates a 3- to 7-membered heteroaromatic ring, a 3- to 7-membered saturated heterocyclic ring or a 3- to 7-membered unsaturated heterocyclic ring, which have 1 to 4 hetero atoms selected from nitrogen atom, oxygen atom and sulfur atom other than carbon atom as an atom constituting the ring, or indicates a condensed heterocyclic ring in which benzene ring and these heterocyclic rings are condensed. For example, aziridine-1-yl group, aziridine-2-yl group;

tetrahydrofuran-2-yl group, tetrahydrofuran-3-yl group, pyrrolidine-1-yl group, pyrrolidine-2-yl group, pyrrolidine-3-yl group;

pyrrol-1-yl group, pyrrol-2-yl group, pyrrol-3-yl group, furan-2-yl group, furan-3-yl group, thiophene-2-yl group, thiophene-3-yl group, imidazole-1-yl group, imidazole-2-yl group, imidazole-4-yl group, imidazole-5-yl group, pyrazole-1-yl group, pyrazole-3-yl group, pyrazole-4-yl group, pyrazole-5-yl group, oxazole-2-yl group, oxazole-4-yl group, oxazole-5-yl group, thiazole-2-yl group, thiazole-4-yl group, thiazole-5-yl group, isoxazole-3-yl group, isoxazole-4-yl group, isoxazole-5-yl group, isothiazole-3-yl group, isothiazole-4-yl group, isothiazole-5-yl group, 1,2,3-triazole-1-yl group, 1,2,3-triazole-4-yl group, 1,2,3-triazole-5-yl group, 1,2,4-triazole-1-yl group, 1,2,4-triazole-3-yl group, 1,2,4-triazole-5-yl group, 1,3,4-oxadiazole-2-yl group, 1, 2, 4-oxadiazole-3-yl group, 1,3,4-thiadiazole-2-yl group, 1,2,4-thiadiazole-3-yl group, tetrazole-1-yl group, tetrazole-2-yl group;

pyridine-2-yl group, pyridine-3-yl group, pyridine-4-yl group, pyrazine-2-yl group, pyrimidine-2-yl group, pyrimidine-4-yl group, pyrimidine-5-yl group, pyridazine-3-yl group, pyridazine-4-yl group, triazinyl group;

indole-1-yl group, indole-2-yl group, indole-3-yl group, indole-4-yl group, indole-5-yl group, indole-6-yl group, indole-7-yl group, benzofuran-2-yl group, benzofuran-3-yl group, benzofuran-4-yl group, benzofuran-5-yl group, benzofuran-6-yl group, benzofuran-7-yl group, benzothiophene-2-yl group, benzothiophene-3-yl group, benzothiophene-4-yl group, benzothiophene-5-yl group, benzothiophene-6-yl group, benzothiophene-7-yl group, isoindole-1-yl group, isoindole-2-yl group, isoindole-4-yl group, isoindole-5-yl group, isoindole-6-yl group, isoindole-7-yl group, isobenzofuran-1-yl group, isobenzofuran-4-yl group, isobenzofuran-5-yl group, isobenzofuran-6-yl group, isobenzofuran-7-yl group, benzimidazole-1-yl group, benzimidazole-2-yl group, benzimidazole-4-yl group, benzimidazole-5-yl group, benzoxazole-2-yl group, benzoxazole-4-yl group, benzoxazole-5-yl group, benzothiazole-2-yl group, benzothiazole-4-yl group, benzothiazole-5-yl group;

chromene-2-yl group, chromene-3-yl group, chromene-4-yl group, chromene-5-yl group, chromene-6-yl group, chromene-7-yl group, chromene-8-yl group, quinoline-2-yl group, quinoline-3-yl group, quinoline-4-yl group, quinoline-5-yl group, quinoline-6-yl group, quinoline-7-yl group, quinoline-8-yl group, isoquinoline-1-yl group, isoquinoline-3-yl group, isoquinoline-4-yl group, isoquinoline-5-yl group, isoquinoline-6-yl group, isoquinoline-7-yl group, isoquinoline-8-yl group;

piperidine-1-yl group, piperidine-2-yl group, piperidine-3-yl group, piperidine-4-yl group, piperazine-1-yl group, piperazine-2-yl group, piperazine-3-yl group, morpholine-2-yl group, morpholine-3-yl group, morpholine-4-yl group;

1,3-benzodioxole-4-yl group, 1,3-benzodioxole-5-yl group, 1,4-benzodioxane-5-yl group, 1,4-benzodioxane-6-yl group, 3,4-dihydro-2H-1,5-benzodioxepine-6-yl group, 3,4-dihydro-2H-1,5-benzodioxepine-7-yl group, 2,3-dihydrobenzofuran-4-yl group, 2,3-dihydrobenzofuran-5-yl group, 2,3-dihydrobenzofuran-6-yl group, 2,3-dihydrobenzofuran-7-yl group; may be cited.

Among these, a 5- to 10-membered heterocyclic group is preferable, and pyrazole-1-yl group, pyrazole-3-yl group, pyrazole-4-yl group, pyrazole-5-yl group, pyridine-2-yl group, pyridine-3-yl group, pyridine-4-yl group, pyrazine-2-yl group, pyrazine-3-yl group are particularly preferable.

The "unsubstituted C1-6 alkyl group" indicates a linear or branched C1-6 alkyl group. For example, methyl group, ethyl group, n-propyl group, n-butyl group, n-pentyl group, n-hexyl group, i-propyl group, i-butyl group, s-butyl group, t-butyl group, isopentyl group, neopentyl group, 2-methyl butyl group, 2,2-dimethyl propyl group, isohexyl group or the like may be cited.

The "unsubstituted C6-10 aryloxy group" indicates a monocyclic or polycyclic C6-10 aryloxy group. For example, phenyloxy group, 1-naphthyloxy group, 2-naphthyloxy group or the like may be cited. Among these, phenoxy group is preferable.

The "unsubstituted C6-10 arylamino group" indicates an amino group substituted by one or two monocyclic or polycyclic C6-10 aryl group. For example, a mono C6-10 acylamino group such as phenylamino group, 4-methyl phenylamino group or the like; a di C6-10 acylamino group such as diphenylamino group, di 1-naphthylamino group or the like may be cited.

The "unsubstituted C1-11 acyl group" indicates a group represented by RCO—. R represents hydrogen atom, a linear or branched C1-6 alkyl group, a linear or branched C2-6 alkenyl group, a liner or branched C2-6 alkynyl group, a monocyclic or polycyclic C6-10 aryl group, or 5- to 7-membered heterocyclic group having 1 to 4 heteroatoms selected from nitrogen atom, oxygen atom and sulfur atom other than carbon atom as an atom constituting the ring. For example, an alkyl carbonyl group such as formyl group, acetyl group, propionyl group, n-propyl carbonyl group, n-butyl carbonyl group, pentanoyl group, valeryl group, i-propyl carbonyl group, i-butyl carbonyl group, pivaloyl group, isovaleryl group or the like; an alkenyl carbonyl group such as acryloyl group, methacryloyl group or the like; an alkynyl carbonyl group such as propioloyl group or the like; an aryl carbonyl group such as benzoyl group, naphthyl carbonyl group or the like; a heterocyclic carbonyl group such as 2-pyridyl carbonyl group, thienyl carbonyl group or the like; benzyl carbonyl group, phenethyl carbonyl group, 2-pyridyl methyl carbonyl group or the like may cited. Among these, a C1-7 acyl group is preferable.

The "unsubstituted (1-imino) C1-6 alkyl group" indicates imino methyl group, or a group in which a linear or branched C1-5 alkyl group bonds to imino methyl group. For example, iminomethyl group, (1-imino)ethyl group, (1-imino)propyl group, (1-imino)butyl group, (1-imino)pentyl group, (1-imino)hexyl group, (1-imino)isobutyl group, (1-imino) isopentyl group, (1-imino)neopentyl group or the like may be cited. Among these, a (1-imino)C1-4 alkyl group is preferable.

The "unsubstituted amino group" indicates $NH_2$ group, the "unsubstituted mercapto group" indicates SH group (thiole group), the "sulfonyl group" indicates $SO_2$ group (sulfone group), the "sulfinyl group" indicates SO group (thionyl group), the "cyano group" indicates CN group, the "nitro group" indicates $NO_2$ group, the "unsubstituted hydroxy group" indicates OH group, and the "unsubstituted benzyl group" indicates benzyl group.

The "halogen group" indicates fluorine atom, chlorine atom, bromine atom, or iodine atom.

As examples of the "tri-substituted silyl group", trimethyl silyl group, triethyl silyl group, tricyclopropyl silyl group, t-butyl dimethyl silyl group or the like may be cited.

The term "substituted" indicates that one or more hydrogen atoms in the above "groups" are substituted by a "substituent". The number of the "substituents" is not particularly limited.

As examples of the "substituent", the above-described "unsubstituted C1-6 alkyl group", "unsubstituted C2-6 alkenyl group", "unsubstituted C2-6 alkynyl group", "unsubstituted C3-6 cycloalkyl group", "unsubstituted C4-8 cycloalkenyl group", "unsubstituted C6-10 aryl group", "unsubstituted heterocyclic group", "unsubstituted C1-11 acyl group", "unsubstituted (1-imino)C1-6 alkyl group", "halogen group" and "silyl group" may be cited, and also "hydroxy group", "amino group", "mercapto group", "sulfonyl group", "sulfinyl group", "cyano group" or "nitro group" may be cited. In these "substituents", one or more hydrogen atoms may be substituted by other "substituents".

Examples of the "substituted groups" are shown in below.

As examples of the "substituted alkyl group", a "C1-6 alkyl group" substituted by a "C3-6 cycloalkyl group" such as cyclopropyl methyl group, 2-cyclopropyl ethyl group, cyclopentyl methyl group, 2-cyclohexyl ethyl group or the like (namely, a "C3-6 cycloalkyl C1-6 alkyl group", preferably a "C3-6 cycloalkyl C1-2 alkyl group");

a "C1-6 alkyl group" substituted by a "C4-6 cycloalkenyl group" such as cyclopentenyl methyl group, 3-cyclopentathenyl methyl group, 3-cyclohexenyl methyl group, 2-(3-cyclohexenyl)ethyl group or the like (namely, a "C4-6 cycloalkenyl C1-6 alkyl group", preferably a "C4-6 cycloalkenyl C1-2 alkyl group");

a "C1-6 alkyl group" substituted by a "halogen group" such as fluoromethyl group, chloromethyl group, bromomethyl group, difluoromethyl group, dichloromethyl group, dibromomethyl group, trifluoromethyl group, trichloromethyl group, tribromomethyl group, 2,2,2-tolufluoroethyl group, 2,2,2-trichloroethyl group, pentafluoroethyl group, 4-fluorobutyl group, 4-chlorobutyl group, 3,3,3-trifluoropropyl group, 2,2,2-trifluoro-1-trifluoromethyl ethyl group, perfluorohexyl group, perchlorohexyl group, 2,4,6-trichlorohexyl group or the like (namely, a "C1-6 haloalkyl group", preferably a "C1-6 haloalkyl group substituted by 1 to 3 halogen atoms", particularly preferably a trifluoromethyl group);

a "C1-6 alkyl group" substituted by a "C6-10 aryl group" such as benzyl group, phenethyl group, 3-phenyl propyl group, 1-naphthyl methyl group, 2-naphthyl methyl group or the like (namely, a "C6-10 aryl C1-6 alkyl group", preferably a "phenyl C1-2 alkyl group");

a "C1-6 alkyl group" substituted by a "heterocyclic group" such as 2-pyridyl methyl group, 3-pyridyl methyl group, 4-pyridyl methyl group, 2-(2-pyridyl)ethyl group, 2-(3-pyridyl)ethyl group, 2-(4-pyridyl)ethyl group, 3-(2-pyridyl)propyl group, 3-(3-pyridyl)propyl group, 3-(4-pyridyl)propyl group, 2-pyrazyl methyl group, 3-pyrazyl methyl group, 2-(2-pyrazyl)ethyl group, 2-(3-pyrazyl)ethyl group, 3-(2-pyrazyl)propyl group, 3-(3-pyrazyl)propyl group, 2-pyrimidyl methyl group, 4-pyrimidyl methyl group, 2-(2-pyrimidyl)ethyl group, 2-(4-pyrimidyl)ethyl group, 3-(2-pyrimidyl)propyl group, 3-(4-pyrimidyl)propyl group, 2-furyl methyl group, 3-furyl methyl group, 2-(2-furyl)ethyl group, 2-(3-furyl) ethyl group, 3-(2-furyl)propyl group, 3-(3-furyl)propyl group or the like (namely, a "heterocyclic C1-6 alkyl group", preferably a "5- to 6-membered heterocyclic C1-2 alkyl group");

a "C1-6 alkyl group" substituted by a "hydroxy group" such as hydroxymethyl group, hydroxyethyl group, hydroxypropyl group or the like (namely, a "hydroxy C1-6 alkyl group", preferably a "hydroxy C1-2 alkyl group"); or the like may be cited.

Among the "substituted alkyl group", as examples of a "substituted alkyl group" in which one or more hydrogen atoms in the substituents is substituted by other "substitutents", a "hydroxy C1-6 alkyl group" substituted by a "C1-6 alkyl group" such as methoxymethyl group, ethoxymethyl group, methoxyethyl group, ethoxyethyl group, methoxy n-propyl group, ethoxymethyl group, ethoxyethyl group, n-propoxymethyl group, i-propoxyethyl group, s-butoxymethyl group, t-butoxyethyl group, 1, 2-dimethoxyethyl group, 2,2-dimethoxyethyl group or the like (namely, a "C1-6 alkoxy C1-6 alkyl group", preferably a "C1-6 alkoxy C1-2 alkyl group");

a "C1-6 alkyl group" substituted by an "oxy group" such as epoxy group, 2,3-epoxypropyl group or the like; a "hydroxy C1-6 alkyl group" substituted by a "C1-11 acyl group" such as formyloxymethyl group, acetoxymethyl group, 2-acetoxyethyl group, propionyloxymethyl group, propionyloxyethyl group or the like (namely, a "C1-11 acyloxy C1-6 alkyl group", preferably a "C2-7 acyloxy C1-2 alkyl group"); and the like may be cited.

As examples of the "substituted C3-6 cycloalkyl group", a "C3-6 cycloalkyl group" substituted by a "C1-6 alkyl group" such as 2,3,3-trimethyl cyclobutyl group, 4, 4,6,6-tetramethyl cyclohexyl group, 1,3-dibutyl cyclohexyl group or the like (namely, a "C1-6 alkyl C3-6 cycloalkyl group", preferably a "C4-6 cycloalkyl group substituted by 1 to 3 C1-2 alkyl groups") may be cited.

As examples of the "substituted C4-8 cycloalkenyl group", a "C4-8 cycloalkenyl group" substituted by a "C1-6 alkyl group" such as 2-methyl-3-cyclohexenyl group, 3,4-dimethyl-3-cyclohexenyl group or the like (namely, a "C1-6 alkyl C-4-6 cycloalkenyl group", preferably a "C4-6 cycloalkenyl group substituted by 1 to 3 C1-2 alkyl groups") may be cited.

As examples of the "substituted C2-6 alkenyl group", a "C2-6 alkenyl group" substituted by a "halogeno group" such as 3-chloro-2-propenyl group, 4-chloro-2-butenyl group, 4,4-dichloro-3-butenyl group, 4,4-difluoro-3-butenyl group, 3,3-dichloro-2-propenyl group, 2,3-dichloro-2-propenyl group, 3,3-difluoro-2-propenyl group, 2,4,6-trichloro-2-hexenyl group or the like (namely, "a C2-6 haloalkenyl group", preferably a "C2-6 haloalkenyl group substituted by 1-3 halogen atoms") may be cited.

As examples of the "substituted C2-6 alkynyl group", a "C2-6 alkynyl group" substituted by a "halogeno group" such as 3-chloro-1-propynyl group, 3-chloro-1-butynyl group, 3-bromo-1-butynyl group, 3-bromo-2-propynyl group, 3-iodo-2-propynyl group, 3-bromo-1-hexynyl group, 5,5-dichloro-2-methyl-3-pentynyl group, 4-chloro-1,1-dimethyl-2-butynyl group (namely, a "C2-6 haloalkynyl group", preferably a "C2-6 haloalkynyl group substituted by 1 to 3 halogen atoms") or the like may be cited.

As examples of the "substituted hydroxy group, a "hydroxy group" substituted by "a C1-6 alkyl group" such as methoxy group, ethoxy group, n-propoxy group, n-butoxy group, n-pentyloxy group, n-hexyloxy group, i-propoxy group, i-butoxy group, s-butoxy group, t-butoxy group, 1-ethyl propoxy group, isohexyloxy group, 4-methyl pentoxy group, 3-methyl pentoxy group, 2-methyl pentoxy group, 1-methyl pentoxy group, 3,3-dimethyl butoxy group, 2,2-dimethyl butoxy group, 1,1-dimethyl butoxy group, 1,2-dimethyl butoxy group, 1,3-dimethyl butoxy group, 2,3-dimethyl butoxy group, 1-ethyl butoxy group, 2-ethyl butoxy group (namely, a "C1-6 alkoxy group") or the like;

a "hydroxy group" substituted by a "C2-6 alkenyl group" such as vinyloxy group, 1-propenyloxy group, 2-propenyloxy group, 1-butenyloxy group, 2-butenyloxy group, 3-butenyloxy group, 1-pentenyloxy group, 2-pentenyloxy group, 3-pentenyloxy group, 4-pentenyloxy group, 1-hexenyloxy group, 2-hexenyloxy group, 3-hexenyloxy group, 4-hexenyloxy group, 5-hexenyloxy group, 1-methyl-2-propenyloxy group, 2-methyl-2-propenyloxy group, 1-methyl-2-butenyloxy group, 2-methyl-2-butenyloxy group (namely, a "C2-6 alkenyloxy group", preferably a "C2-4 alkenyloxy group") or the like;

a "hydroxy group" substituted by a "C2-6 alkynyl group" such as ethynyloxy group, propynyloxy group, propargyloxy group, 1-butynyloxy group, 2-butynyloxy group, 3-butynyloxy group, 1-pentynyloxy group, 2-pentynyloxy group, 3-pentynyloxy group, 4-pentynyloxy group, 1-hexynyloxy group, 1-methyl-2-propynyloxy group, 2-methyl-3-butynyloxy group, 1-methyl-2-butynyloxy group, 2-methyl-3-pentynyloxy group, 1,1-dimethyl-2-butynyloxy group (namely, a "C2-6 alkynyloxy group", preferably a "C2-4 allynyloxy group") or the like;

a "hydroxy group" substituted by a "C3-6 cycloalkyl group" such as cyclopropyloxy group, cyclobutyloxy group, cyclopentyloxy group, cyclohexyloxy group (namely, a "C3-6 cycloalkoxy group") or the like;

a "hydroxy group" substituted by a "C1-11 acyl group" such as acetyloxy group, propionyloxy group, n-propyl carbonyloxy group, i-propyl carbonyloxy group, n-butyl carbonyloxy group, i-butyl carbonyloxy group, pentanoyloxy group, pivaloyloxy group (namely, a "C1-11 acyloxy group", preferably a "C1-7 acyloxy group") or the like;

a "hydroxy group" substituted by "silyl group" such as trimethyl silyloxy group, triethyl silyloxy group, t-butyl dimethyl silyloxy group (namely, "silyloxy group") or the like; or the like may be cited.

Among the "substituted hydroxyl group", as examples of a "substituted hydroxyl group" in which one or more hydrogen atoms in the substituents is substituted by other "substituents", a "C1-6 alkoxy group" substituted by an "optionally substituted C3-6 cycloalkyl group" or an "optionally substituted C6-10 aryl group" as the other "substituent" such as cyclopropyl methyloxy group, 2-cyclopentyl ethyloxy group, benzyloxy group or the like;

a "C1-6 alkoxy group" substituted by a "halogen group" as the other "substituent" such as chloromethoxy group, dichloromethoxy group, trichloromethoxy group, trifluoromethoxy group, 1-fluoroethoxy group, 1,1-difluoroethoxy group, 2,2,2-trifluoroethoxy group, pentafluoroethoxy group (namely, a "C1-6 haloalkoxy group", preferably a "C1-6 haloalkoxy group substituted by 1-3 halogen atoms") or the like;

a "C3-6 cycloalkoxy group" substituted by an "optionally substituted C1-6 alkyl group" as the other "substituent" such as 2-methyl cyclopropyloxy group, 2-ethyl cyclopropyloxy group, 2,3,3-trimethyl cyclobutyloxy group, 2-methyl cyclopentyloxy group, 2-ethyl cyclohexyloxy group (preferably, a "C3-6 cycloalkoxy group") or the like; or the like may be cited.

As examples of the "substituted acyl group", a C1-11 acyl group substituted by a "halogen group" such as monofluoroacetyl group, monochloroacetyl group, monobromoacetyl group, difluoroacetyl group, dichloroacetyl group, dibromoacetyl group, trifluoroacetyl group, trichloroacetyl group, tribromoacetyl group, 3,3,3-trifluoropropionyl group, 3,3,3-trichloropropionyl group, 2,2,3,3,3-pentafluoropropionyl group (namely, a "C1-11 haloacyl group", preferably a "C2-7 haloacyl group substituted by 1-3 halogen atoms") or the like;

a C1 acyl group substituted by a "hydroxy group" such as acetoxyl group, propyoxyl group (namely, carboxyl group) or the like;

a C1 acyl group substituted by an "amino group" (namely, "carbamoyl group"); or the like may be cited.

Among the "substituted acyl group", as examples of a "substituted acyl group" in which one or more hydrogen atoms in the substitutents is substituted by other "substituents", a "carboxyl group" substituted by a "C1-6 alkyl group" such as methoxycarbonyl group, ethoxycarbonyl group, n-propoxycarbonyl group, i-propoxycarbonyl group, n-butoxycarbonyl group, i-butoxycarbonyl group, t-butoxycarbonyl group, n-pentyloxycarbonyl group, n-hexyloxycarbonyl group, decyloxycarbonyl group (namely, a "C1-6 alkoxycarbonyl group") or the like;

a "C1-6 alkoxycarbonyl group" substituted by a "C3-6 cycloalkyl group" or a "C6-10 aryl group" as the other "substituent" such as cyclopropyl methyloxycarbonyl group, 2-cyclopentyl ethyloxycarbonyl group, benzyloxycarbonyl group or the like;

a "carbamoyl group" substituted by an "alkyl group" such as methyl carbamoyl group, ethyl carbamoyl group, dimethyl carbamoyl group, diethyl carbamoyl group (preferably a "mono C1-6 alkyl carbamoyl group" or a "di C1-6 alkyl carbamoyl group") or the like;

a "mono C6-10 aryl carbamoyl group" such as phenyl carbamoyl group, 4-methyl phenyl carbamoyl group or the like;

a "C1-7 acyl carbamoyl group" such as acetyl carbamoyl group, benzoyl carbamoyl group or the like; may be cited.

As examples of the "substituted (1-imino)C1-6 alkyl group", a "(1-imino)C1-6 alkyl group" substituted by a "hydroxy group" such as hydroxyiminomethyl group, (1-hydroxyimino)ethyl group, (1-hydroxyimino)propyl group, (1-hydroxyimino)butyl group (namely, "(1-hydroxyimino)C1-6 alkyl group", preferably a "(1-hydroxyimino)C1-4 alkyl group") or the like;

a (1-hydroxyimino)C1-6 alkyl group substituted by a C1-6 alkyl group as the other "substituent" such as methoxyiminomethyl group, (1-ethoxyimino)methyl group, (1-ethoxyimino)ethyl group (namely, "(1-(C1-6 alkoxy)imino)C1-6 alkyl group", preferably "(1-(C1-6 alkoxy)imino)C1-4 alkyl group") or the like may be cited.

As examples of the "substituted amino group", an "amino group ($NH_2$ group)" substituted by a "C1-6 alkyl group" such as methylamino group, ethylamino group, dimethylamino group, diethylamino group (preferably a mono C1-6 alkylamino group or a di C1-6 alkylamino group) or the like;

an "amino group ($NH_2$ group)" substituted by an "alkylidene group" such as methylidene amino group, ethylidene amino group (preferably a "mono C1-6 alkylidene amino group") or the like;

a "C1-7 acylamino group" such as formylamino group, acetylamino group, benzoylamino group or the like may be cited.

As examples of the "substituted mercapto group", a "mercapto group" substituted by an "alkyl group" such as methyl thio group, ethyl thio group (preferably a "C1-6 alkyl thio group") or the like;

a C6-10 aryl thio group such as phenyl thio group, 4-methyl phenyl thio group or the like;

a C1-7 acyl thio group such as acetyl thio group, benzoyl thio group or the like; may be cited.

As examples of the "substituted sulfonyl group", a sulfonyl group substituted by an "alkyl group" such as methyl sulfonyl group, ethyl sulfonyl group, n-propyl sulfonyl group, isopropyl sulfonyl group, n-butyl sulfonyl group, isobutyl sulfonyl group, s-butyl sulfonyl group, t-butyl sulfonyl group, n-pentyl sulfonyl group, isopentyl sulfonyl group, neopentyl sulfonyl group, 1-ethyl propyl sulfonyl group, n-hexyl sulfonyl group, isohexyl sulfonyl group (preferably a C1-6 alkyl sulfonyl group) or the like;

a C1-6 haloalkyl sulfonyl group such as trifluoromethyl sulfonyl group or the like;

a C6-10 aryl sulfonyl group such as phenyl sulfonyl group, 4-methyl phenyl sulfonyl group or the like;

a sulfo group ($SO_3H$ group);

a C1-6 alkoxysulfonyl group such as methoxysulfonyl group, ethoxysulfonyl group or the like;

sulfamoyl group;

a sulfamoyl group such as N-methyl sulfamoyl group, N-ethyl sulfamoyl group, N,N-dimethyl sulfamoyl group, N,N-diethyl sulfamoyl group (preferably, a mono C1-6 alkyl sulfamoyl group or a di C1-6 allyl sulfamoyl group) or the like;

a mono C6-10 aryl sulfamoyl group such as phenyl sulfamoyl group, 4-methyl phenyl sulfamoyl group or the like; may be cited.

As examples of the "substituted sulfinyl group", a sulfinyl group substituted by a "C1-6 alkyl group" such as methyl sulfonyl group, ethyl sulfinyl group, n-propyl sulfinyl group, isopropyl sulfinyl group, n-butyl sulfinyl group, isobutyl sulfinyl group, s-butyl sulfinyl group, t-butyl sulfinyl group, n-pentyl sulfinyl group, isopentyl sulfinyl group, neopentyl sulfinyl group, 1-ethyl propyl sulfinyl group, n-hexyl sulfinyl group, isohexyl sulfinyl group (preferably, a C1-6 alkyl sulfinyl group) or the like;

a C1-6 haloalkyl sulfinyl group such as trifluoromethyl sulfinyl group or the like;

a C6-10 aryl sulfinyl group such as phenyl sulfinyl group, 4-methyl phenyl sulfinyl group or the like; may be cited.

As examples of the "substituted C6-10 aryl group", a C6-10 aryl group substituted by a halogen atom such as 2-chlorophenyl group, 3,5-difluorophenyl group or the like, a C6-10 aryl group substituted by a C1-6 alkyl group such as 3-methyl phenyl group, 4-isopropyl-1-naphthyl group or the like may be cited.

As examples of the "substituted benzyl group", 4-chlorobenzyl group, 4-trifluoromethyl benzyl group or the like may be cited.

As examples of the "substituted heterocyclic group", 3-chloro-1-pyridyl group, 3-methyl-2-thienyl group or the like may be cited.

As examples of the "substituted C6-10 aryloxy group, a C6-10 aryloxy group substituted by a halogen atom such as 2-chlorophenoxy group, 3,5-difluorophenoxy group or the like, a C6-10 aryloxy group substituted by a C1-6 alkyl group such as 3-methyl phenoxy group, 4-isopropyl-1-naphthyloxy group or the like may be cited.

As examples of the "substituted C6-10 arylamino group, a C6-10 arylamino group substituted by a halogen atom such as 2-chlorophenylamino group, 3,5-difluorophenylamino group or the like, a C6-10 arylamino group substituted by a C1-6 alkyl group such as 3-methyl phenylamino group, 4-isopropyl-1-naphthylamino group or the like may be cited.

In formula (1), n represents an integer of 1 to 4. The chemical formulas corresponding to n are shown below.

[Chemical formula 6]

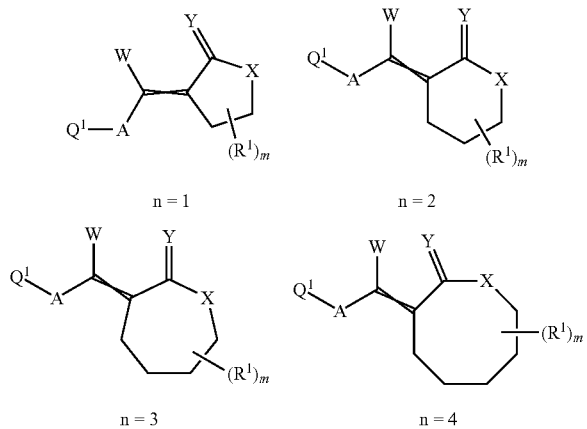

[Chemical formula 7]

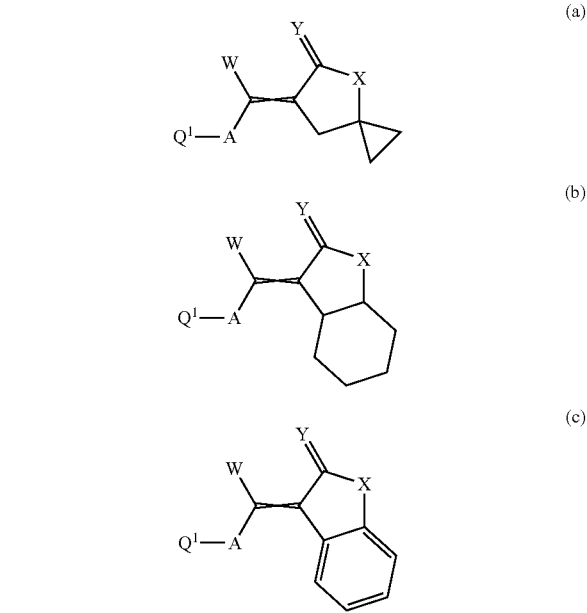

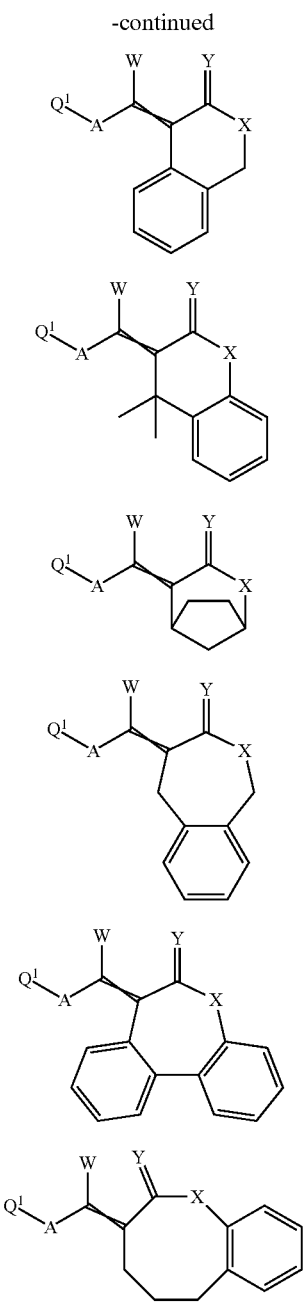

m represents an integer of 0 to 10, when m is 2 or more, $R^1$ may be the same or different from each other, and more than one $R^1$ may bond together to form an optionally substituted 3- to 8-membered ring.

As examples of the compound, in which more than one $R^1$ bond together to form an optionally substituted 3- to 8-membered ring, the following compounds (a) to (i) may be cited.

A compound represented by formula (2) is a preferable aspect of 1-heterodienen derivative of the present invention.

The compound represented by formula (2) is the same as a compound represented by formula (1), where Y represents N-$Q^3$ ($Q^3$ represents an optionally substituted phenyl group), $Q^1$ represents an optionally substituted phenyl group, X represents $X^1$.

The salt of 1-heterodien derivative of the present invention is a horticulturally permissible salt of the compound represented by formulas (1) and (2). For example, a salt of inorganic acid such as hydrochloride salt, sulfate salt or the like; a salt of organic acid such as acetic acid, lactic acid or the like; a salt of alkali metal such as lithium, sodium, potassium or the like; a salt of alkali earth metal such as calcium, magnesium, or the like; a salt of transition metal such as iron, copper or the like; a salt of organic base such as ammonia, triethylamine, tributylamine, pyridine, hydrazine or the like may be cited.

Hereafter, the 1-heterodiene derivative and salt thereof of the present invention will be described in more detail using production examples of the 1-heterodiene derivative represented by formula (1). In addition, the following production examples are only to describe the present invention, and do not limit the scope of the present invention.

[Production Example of the Compound Represented by Formula (1), where Y Represents N-$Q^3$ (Imidate Compound (E))]

An imidate compound (E) which is one of the compounds of the present invention will be described below with reference to the following chemical reaction formulas.

Oxymethylidene chain is introduced into a starting material of a compound (A) using desired esters, and the resulting compound is sulfonated, thereby obtaining a compound (B). Then, a compound (C) is obtained by adding a compound represented by $Q^1$-A-H. Then, a compound (D) is obtained by an addition reaction with a compound represented by $Q^3$-$NH_2$. Lewis acid may be added if needed.

The imidate compound (E) of the present invention is obtained by reacting the compound (D) with a dehydration condensation agent such as methanesulfonyl chloride (MsCl) in the presence of a base.

In addition, a compound (E), where X represents sulfur atom may be obtained using a suitable sulfur source in the middle step. Examples of the sulfur source may cite phosphorus pentasulfide, Lawesson reagent or the like.

In addition, in the following chemical reaction formulas, the definitions of $Q^1$, $Q^3$, W, A, m, n and X are the same as defined in formula (1). R' represents a C1-6 alkyl group. $R^{11}$ is the same as $R^1$ of formula (1) or represents substituents which are able to convert to $R^1$ by a general synthesis method. R" represents a C1-6 alkyl group or a phenyl group which may be substituted by a C1-6 alkyl group or a halogen atom.

[Chemical formula 8]

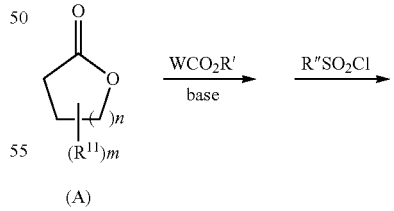

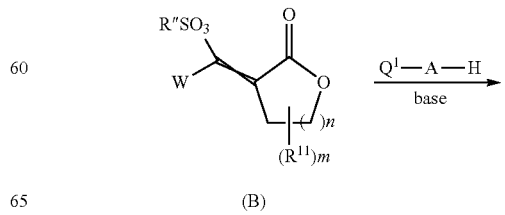

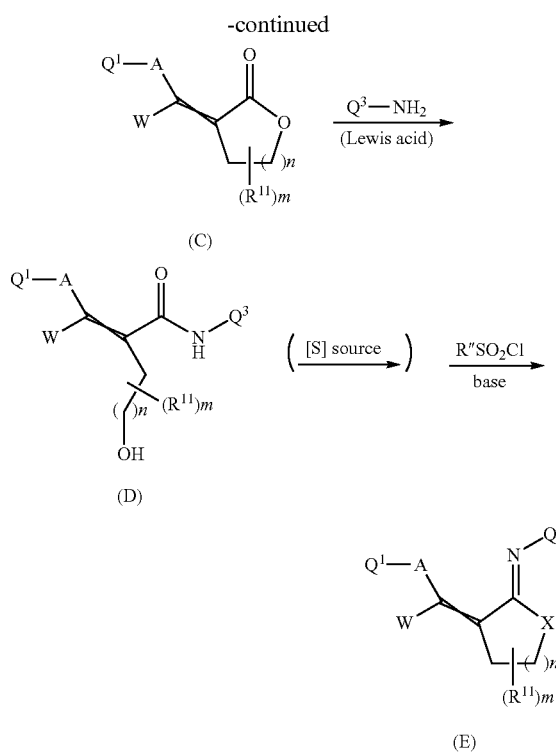

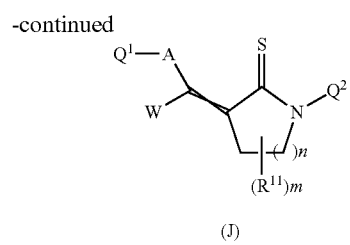

Oxymethylidene chain is introduced using desired esters into a compound (F), which can be synthesized by a conventional method, and the resulting compound is sulfonated, thereby obtaining a compound (G). Then, a lactam compound (H), which is one of the compounds of the present invention is obtained by adding a compound represented by $Q^1$-A-H.

Furthermore, a compound (J), which is one of the compounds of the present invention may be obtained using a suitable sulfur source. Examples of the sulfur source may cite phosphorus pentasulfide or Lawesson reagent.

In addition, in the above chemical reaction formulas, definitions of $Q^1$, $Q^2$, W, A, m and n are the same as defined in formula (1). The definitions of R', $R^{11}$ and R" are the same as described above.

[Production Example of Compound Represented by Formula (1), where X Represents N-$Q^2$ (Lactam Compound (K))]

The production method of the lactam compound (K) of the present invention will be described with reference to the following chemical reaction formula.

[Production Example of Compound Represented by Formula (1), where X Represents N-$Q^2$ (Lactam Compounds (H) and (J))]

The production method of lactam compounds (H) and (J) of the present invention will be described with reference to the following chemical reaction formulas.

[Chemical formula 9]

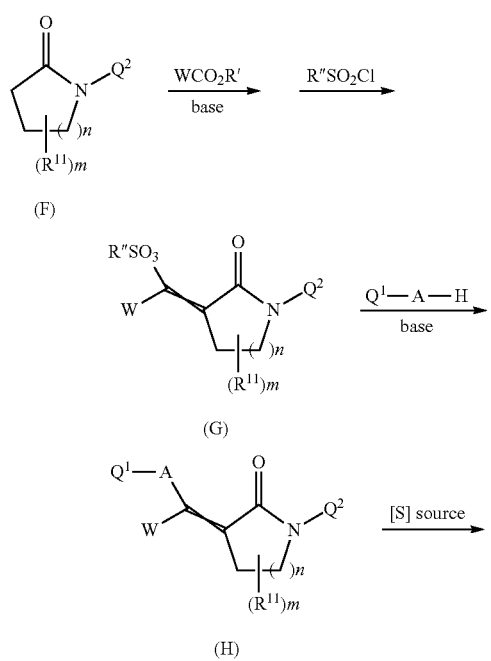

[Chemical formula 10]

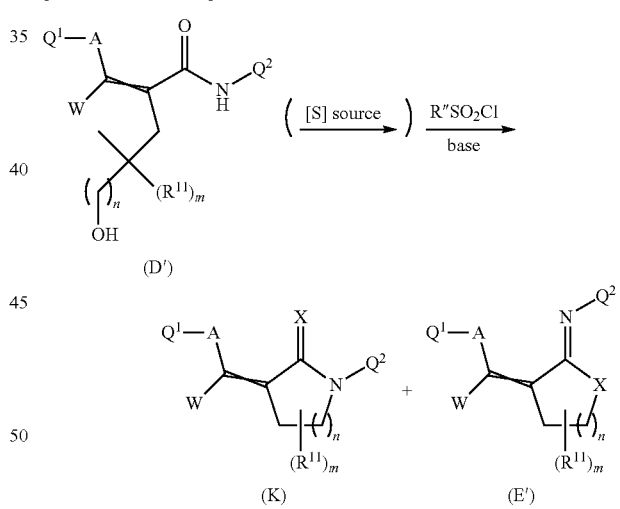

In addition, in the above-described chemical formula, the definitions of $Q^1$, $Q^2$, W, A, m and n are the same as defined in formula (1). The definitions of R11 and R" are the same as described above.

A compound (D') is synthesized according to the production method of the imidate compound (E). The lactam compound (K), which is one of the compounds of the present invention is obtained by reacting with a dehydration condensation agent such as MsCl or the like in the presence of a base.

In some cases, an imidate compound (E'), which is one of the compounds of the present invention may also be obtained at the same time. In addition, the compound (K), where X represents sulfur atom may be obtained by adding a suitable sulfur source in the middle step. Examples of the sulfur source may cite phosphorus pentasulfide or Lawesson reagent.

In either of these reactions, if purification of the product is required after the completion of the reaction, known, commonly used purification means such as distillation, recrystallization or column chromatography, can be employed following carrying out of an ordinary post-treatment operation.

The structure of the intended compound can be identified and confirmed by known analysis means such as elementary analysis, NMR spectroscopy, IR spectroscopy or mass spectrometry.

The compound of the present invention may be used for control of agricultural crop pest, mite, hygiene pest, grain-storage insect, textile pest, household pest or the like, since the compound has an insecticidal effect on adults, nymphs, larvae and has an ovicidal effect.

Examples of the control target of the organisms are shown below.

Lepidopteran pests such as, for example, *Spodoptera litura, Mamestra brassicae, agrotis ipsilon*, green caterpillars, *Autographa nigrisigna, Plutella xylostella, Adoxophyes honmai, Homona magnanima, Carposina sasakii, Grapholita molesta, Phyllocnistis citrella, Caloptilia theivora, Phyllonorycter ringoniella, Lymantria dispar, Euproctis pseudoconspersa, Chilo suppressalis, Cnaphalocrocis medinalis, Ostrinia nubilasis, Hyphantria cunea, Cadra cautella*, genus *Heliothis*, genus *Helicoverpa*, genus *Agrothis, Tinea translucens, Cydia pomonella*, and *Pectinophora gossypiella*;

hemipteran pests such as, for example, *Myzus persicae, Aphis gossypii, Lipaphis erysimi, Rhopalosiphum padi, Riptortus clavatus, Nezara antennata, Unaspis yanonensis, Pseudococcus comstocki, Trialeurodes vaporariorum, Bemisia tabaci, Bemisia argentifolii, Psylla pyrisuga, Stephanitis nashi, Nilaparuata lugens, Laodelphax stratella, Sogatella furcifera*, and *Nephotettix cincticeps*;

coleopteran pests such as, for example, *Phyllotreta striolata, Aulacophora femoralis, Leptinotarsa decemlineata, Lissorhoptrus oryzophilus, Sitophilis zeamais, Callosobruchus chinensis, Popillia japonica, Anomala rufocuprea*, genus *Diabrotica, Lasioderma serricorne, Lyctus brunneus, Monochamus alternatus, Anoplophora malasiaca*, genus *Agriotis, Epilachna vigintioctopunctata, Tenebroides mauritanicus*, and *Anthonomus grandis*;

dipteran pests such as, for example, *Musca domestica, Calliphora lata, Boettcherisca peregrine, Zeugodacus cucurbitae, Bactrocera dorsalis, Delia platura, Agromyza oryzae, Drosophila melanogaster, Stomoxys calcitrans, Culex tritaeniorhynchus, Aedes aegypti*, and *Anopheles sinensis*;

thysanopteran pests such as, for example, *Thrips palmi*, and *Scirtothrips dorsalis*;

hymenopteran pests such as, for example, *Monomorium pharaonis, Vespa simillima xanthoptera*, and *Athalia rosae ruficornis*;

orthopteran pests such as, for example, *Locusta migratoria, Blattella germanica, Periplaneta americana*, and *Periplaneta fuliginosa*;

isopteran pests such as, for example, *Coptotermes formosanus* and *Reticulitermes speratus*;

siphonapteran pests such as, for example, *Pulex irritans* and *Ctenocephalides felis*; phthirapteran pests such as, for example, *Pediculus humanus*;

Acarina such as *Tetranychus urticae, Tetranychus cinnabarinus, Tetranychus kanzawai, Panonychus citri, Panonychus ulmi, Aculops pelekassi, Aculus schlechtendali, Polyphagotarsonemus latus*, genus *Brevipalpus*, genus *Eotetranichus, Rhizoglyphus robini, Tyrophagus putrescentiae, Dermatophagoides farinae, Boophilus microplus*, and *Haemaphysalis longicornis*; and plant parasitic nematodes such as *Meloidogyne incognita, Pratylenchus* spp., *Heterodera glycines, Aphelenchoides besseyi*, and *Bursaphelenchus xylophilus*.

Pests to which application is preferable are lepidopteran pests, hemipteran pests, acarina, thysanopteran pests, and coleopteran pests.

In recent years, the resistance of many pests such as diamondback moths, planthoppers, leafhoppers and aphids to organophosphorous agents, carbamate agents and miticides has grown, the impotency of such chemical agents has become problematic, and there has been increasing demand for chemical agents that are effective relative to resistant strains of pests and mites. The compounds of the present invention are chemical agents that have an excellent pesticidal and miticidal effects not only relative to susceptible strains, but also relative to strains of pests that are resistant to organophosphorous agents, carbamate agents, and pyrethroid agents, as well as strains of mites that are resistant to miticidal agents.

Moreover, the compound of the present invention is a chemical agent that has few harmful effects, low toxicity relative to fish and mammals, and high stability.

The pest control agent of the present invention contains as an active ingredient the compound represented by a formula (1) or (2) of the present invention.

The compound represented by formula (1) or (2) may be used alone or in combination of two or more.

When the compounds of the present invention are practically applied, the compounds may be used without addition of other components, but they are normally further mixed with a solid carrier, liquid carrier, or gaseous carrier, or impregnated into a base material such as porous ceramic sheet or non-woven cloth, with addition of surfactants and other adjuvants as necessary, and formulated for use in a form that can be assumed by common agrochemicals for the purpose of use as an agrochemical, that is, a form such as a wettable powder, granular agent, dust agent, emulsion agent, water-soluble agent, suspension agent, granular wettable powder, flowable, aerosol, smoke and misting agent, heat steam agent, fumigant, poison bait, or microcapsule.

Additives and carriers which may be employed in the case where a solid formulation is desired include vegetable powders such as soybean or wheat flour and the like; mineral micropowders such as diatom clay, apatite, plaster, talc, bentonite, pyrophyllite, clay, and the like; organic and inorganic compounds such as benzoate soda, urea, Glauber's salt, and the like. Solvents which may be employed in the case where a liquid agent is desired include petroleum distallates such as kerosene, xylene, solvent naphtha and the like; cyclohexane, cyclohexanone, dimethylformamide, dimethylsulfoxide, alcohol, acetone, methylisobutylketone, mineral oil, vegetable oil, water, and the like. As a gas carrier which may be employed in the spray agent, one may use butane gas, LG, dimethyl ether, and carbon dioxide gas.

As a base material for poison bait, one may use, for example, bait ingredients such as grain flour, vegetable oil, sugar, and crystalline cellulose; antioxidants such as dibutylhydroxytoluene and nordihydroguacetic acid; preservatives such as dehydroacetic acid; agents which prevent children and pets from eating by mistake such as powdered *capsicum*; and vermin attracting perfumes such as cheese perfume and onion perfume.

Surfactants may be added as necessary in order to achieve a uniform and stable morphology in these formulations.

There are no particular limitations on surfactants, and one may cite, for example, nonionic surfactants such as alkyl ether to which polyoxyethylene is added, higher fatty acid ester to which polyoxyethylene is added, sorbitan higher fatty acid ester to which polyoxyethylene is added, and tristyrylphenyl ether to which polyoxyethylene is added, sulfate ester salt of alkylphenyl ether to which polyoxyethylene is added, alkylnaphthalene sulfonate, polycarboxylate, lignin sulfonate, formaldehyde condensate of alkyl naphthalene sulfonate, copolymer of isobutylene-maleic anhydride, and the like.

In the case where the compound of the present invention is to be used for an agricultural pest control agent, the amount of active ingredient is preferably 0.01 to 90 weight %, and particularly preferably 0.05 to 85 weight %. The formulation such as a wettable powder, emulsion agent, suspension agent, flowable agent, water-soluble agent or granular wettable powder may be used by diluting to a prescribed concentration to obtain a solution, suspension or emulsion and spraying them on plants or soil, or in the case of a dust formulation or granular formulation, it may be used by directly spraying them on plants or soil.

In the case where the compound of the present invention is used as a pest control agent for the prevention of epidemics, the formulation may be prepared as an emulsion agent, wettable powder, flowable agent, or the like, and these formulations may be applied after dilution with water to a prescribed concentration. In the case where the formulation is prepared as an oil agent, aerosol, smoke and misting agent, poison bait, mite control sheet, or the like, it may be directly applied.

In the case where compounds of the present invention are used as pest control agents for the control of external parasites of animals such as livestock including cows and pigs, or pets including dogs and cats, the formulations of compounds of the present invention are used by methods known to those skilled in the veterinary art. With respect to these methods, in the case where, for example, systemic control is desired, one may cite methods of administration by tablet, capsule, immersion fluid, feed intermixture, suppository, injection (intramuscular, subcutaneous, intravenous, intraperitoneal, and so on), and the like; in the case where non-systemic control is desired, one may cite methods of administration of oleaginous or aqueous solutions by spray, pour-on, spot-on, and the like; as well as methods of application of resin formulations molded into an appropriate shape such as a collar or ear tag. In these cases, normally, compounds of the present invention may be used in a proportion of 0.01 to 1000 mg relative to 1 kg of a host animal.

It goes without saying that a compound of the present invention is sufficiently effective when used alone, and it may also be used in a mixture or combination with one or more other types of pest control agent, bactericide, insecticide/miticide, herbicide, plant growth regulation agent, synergist, fertilizer, soil improver, animal feed, and so on.

Representative examples of active ingredients of bactericides, insecticides/miticides, plant growth regulation agents, and the like which can be mixed or combined with a compound of the present invention are shown below.

Germicides:

captan, folpet, thiuram, ziram, zineb, maneb, mancozeb, propineb, polycarbamate, chlorothalonin, quintozene, captafol, iprodione, procymidone, fluoroimide, mepronil, flutolanil, pencycuron, oxycarboxin, fosetyl-aluminum, propamocarb, triadimefon, triadimenol, propiconazole, diclobutrazol, bitertanol, hexaconazole, myclobutanil, flusilazole, etaconazole, fluotrimazole, flutriafen, penconazole, diniconazole, cyproconazole, fenarimol, triflumizole, prochloraz, imazalil, pefurazoate, tridemorph, fenpropimorph, triforine, buthiobate, pyrifenox, anirazine, polyoxins, metalaxyl, oxadixyl, furalaxyl, isoprothiolane, probenazole, pyrrolnitrin, blasticidin S, kasugamycin, validamycin, dihydrostreptomycin sulfate, benomyl, carbendazim, thiophanate-methyl, hymexazol, basic copper chloride, basic copper sulfate, fentinacetate, triphenyltin hydroxide, diethofencarb, chinomethionat, binapacryl, lecithin, baking soda, dithianon, dinocap, fenaminosulf, diclomezine, guazatine, dodine, IBP, edifenphos, mepanipyrim, fermzone, trichlamide, methasulfocarb, fluazinam, ethoquinolac, dimethomorph, pyroquilon, tecloftalam, phthalide, phenazine oxide, thiabendazole, tricyclazole, vinclozolin, cymoxanil, cyclobutanil, guazatine, propamocarb hydrochloride, oxolinic acid, cyflufenamid, iminoctadine, kresoxim-methyl, triazine, fenhexamid, cyazofamid, cyprodinil, prothioconazole, fenbuconazole, trifloxystrobin, azoxystrobin, hexaconazole, imibenconazole, tebuconazole, difenoconazole, and carpropamid;

Insecticides, Miticides:

organic phosphate ester compounds such as profenofos, dichlorvos, fenamiphos, fenitrothion, EPN, diazinon, chlorpyrifos-methyl, acephate, prothiofos, fosthiazate, phosphocarb, cadusafos, disulfoton, chlorpyrifos, demeton-S-methyl, dimethoate, parathion, BRP, CVMP, CVP, CYAP, DEP, MPP, PAP, isofenphos, ethion, ethoprophos, quinalphos, chlorpyrifos, dimethylvinphos, sulprofos, thiometon, vamidothion, pyraclofos, pyridaphenthion, pirimiphos-methyl, propaphos, phosalone, formothion, malathion, tetrachlovinphos, chlorfenvinphos, cyanophos, trichlorfon, methidathion, phenthoate, ESP, azinphos-methyl, fenthion, heptenophos, methoxychlor, malation, monocrotophos or AKD-3088;

carbamate compounds such as carbaryl, propoxur, aldicarb, carbofuran, thiodicarb, methomyl, oxamyl, ethiofencarb, pirimicarb, fenobucarb, carbosulfan, benfuracarb, MIPC, MPMC, MTMC, alanycarb, pyridaphenthion, pirimiphosmethyl, fenothiocarb, furathiocarb, bendiocarb, or XMC;

nereistoxin derivatives such as cartap, thiocyclam or bensultap;

organic chlorine compounds such as dicofol, tetradifon, endosulufan, dienochlor and dieldrin; organic metal compounds such as fenbutatin oxide and cyhexatin;

pyrethroid compounds such as fenvalerate, permethrin, cypermethrin, deltamethrin, cyhalothrin, tefluthrin, ethofenprox, cyfluthrin, fenpropathrin, bifenthrin, Acrinathrin, Allethrin, cycloprothrin, cyfluthrin, halfenprox, flucythrinate or resmethrin; benzoylurea compounds such as diflubenzuron, chlorfluazuron, teflubenzuron, flufenoxuron, lufenuron, novaluron, triflumuron, hexaflumuron, noviflumuron, bistrifluoron, noviflumuron or triflumuron;

juvenile hormone-like compounds such as methoprene, pyriproxyfen, fenoxycarb and diofenolan;

pyridazinone compounds such as pyridaben;

pyrazole compounds such as fenpyroximate, fipronil, tebufenpyrad, ethipyrole, tolfenpyrad, acetoprole, pyrafluprole or pyriprole; neonicotinoids such as imidacloprid, nitenpyram, acetamiprid, thiacloprid, thiamethoxam, clothianidin or dinotefuran;

hydrazine compounds such as tebufenozide, methoxyfenozide, chromafenozide, and halofenozide; dinitro compounds, organic sulfur compounds, urea compounds, triazine compounds, hydrazone compounds;

other compounds such as flonicamid, buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, flufenerim, pyridalyl, spirodiclofen, bifenazate, spiromesifen, spirotetramat, propargite, clofentezine, fluacrypyrim, metaflumizone, flubendiamide, cyflumetofen, chlorantraniliprole, cyenopyrafen, NNI-0101, fenazaquin, metaflumizone, amidoflumet, CL900167, DCIP, phenisobromolate, benzoate, metaldehyde, chlorantraniliprole, spinetoram or pyrifluquinazone;

antibiotics or semisynthetic antibiotics such as abamectin, emamectin benzoate, milbemectin, spinosad, ivermectin, lepimectin;

natural products such as azadirachtin and rotenone;

further, microbial agricultural chemicals such as BT agent, insect viruses, etomopathogenic fungi or nematophagous fungi;

Plant Growth Regulators:

abscisic acid, indolebutyric acid, uniconazole, ethychlozate, ethephon, cloxyfonac, chlormequat, *chlorella* extract, calcium peroxide, cyanamide, dichlorprop, gibberellin, daminozide, decyl alcohol, trinexapac-ethyl, mepiquat chloride, paclobutrazol, paraffin, wax, piperonylbutoxide, pyraflufen-ethyl, flurprimidol, prohydrojasmon, prohexadione calcium salt, benzylaminopurine, pendimethalin, forchlodenuron, maleic hydrazide potassium, 1-naphthylacetoamide, 4-CPA, MCPB, choline, oxyquinoline sulfate, ethychlozate, butoralin, 1-methylcyclopropene, aviglycine hydrochloride.

EXAMPLE

Hereafter, the present invention will be described in detail using the examples. However, the present invention is not limited to the Examples.

Example 1

Production of (Z)—N-((E)-3-(phenylthiomethylene) dihydrothiophen-2(3H)-ylidene) aniline and 1-phenyl-3-(1-(phenylthio)ethylidene)pyrrolidine-2-thione Step 1

Synthesis of (E)-4-hydroxy-N-phenyl-2-(phenylthiomethylene)butanamide 5.2 ml of diethyl aluminium (1 mol/l of hexane solution) was added to 10 ml of methylene chloride solution including 0.49 g of aniline at room temperature.

15 minutes after, 5 ml of methylene chloride solution including 0.9 g of (E)-3-(phenylthiomethylene)dihydrofuran-2(3H)-one synthesized according the method described in non-patent document J. Med. Chem. 1981, 24, pp 468 was dropped into the resulting solution. The solution was stirred at room temperature for 2 hours, followed by adding 10% hydrochloric acid. The resulting solution was filtered using ethyl acetate, and the organic layer was washed with brine, dried with anhydrous magnesium sulfate, filtered, and concentrated under reduced pressure. The residue was purified by silica gel column chromatography to obtain 1.27 g of the title compound.

$^1$H-NMR of the obtained compound is shown below:
$^1$H-NMR (CDCl$_3$) δ ppm: 2.76 (t, 2H), 3.96 (t, 2H), 7.07 (t, 1H), 7.25-7.55 (m, 10H), 9.00 (brs, 1H)

Step 2

Synthesis of (E)-4-(tert-butyl dimethylsilyloxy)-N-phenyl-2-(phenylthiomethylene) butanamide 2 ml of methylene chloride solution including 0.79 g of chloro t-butyl dimethylsilane was dropped into 6 ml of methylene chloride solution including 1.20 g of (E)-4-hydroxy-N-phenyl-2-(phenylthiomethylene)butanamide and 0.63 g of imidazole at room temperature. The resulting solution was stirred at room temperature for 2 hours and added with water, then filtered using ethyl acetate. The organic layer was washed with water 3 times, then washed with brine, and dried with anhydrous magnesium sulfate, filtered, and concentrated under reduced pressure. The residue was purified by silica gel column chromatography to obtain 1.63 g of the title compound.

$^1$H-NMR of the obtained compound is shown below:
$^1$H-NMR (CDCl$_3$) δ ppm: 0.10 (s, 6H), 0.91 (s, 9H), 2.79 (t, 5.4 Hz, 2H), 4.99 (t, 5.4 Hz, 2H), 7.08 (t, 7.4 Hz, 1H), 7.26-7.39 (m, 5H), 7.46 (d, 7.4 Hz, 2H), 7.56 (d, 8.3 Hz, 2H), 7.68 (s, 1H), 8.89 (brs, 1H)

Step 3

Synthesis of (E)-4-(tert-butyldiphenylsilyloxy)-N-phenyl-2-(phenylthiomethylene) butanethioamide 1.11 g of Lawesson reagent was added to 20 ml of tetrahydrofuran solution including 1.63 g of (E)-4-(tert-butyldimethylsilyloxy)-N-phenyl-2-(phenylthiomethylene) butanamide The resulting solution was heated under reflux for one night and cooled to room temperature, followed by adding saturated sodium bicarbonate water to extract. The water layer was extracted with ethyl acetate, and the organic layer was mixed and dried with anhydrous magnesium sulfate, and filtered, and then concentrated under reduced pressure. The residue was purified by silica gel column chromatography to obtain 0.91 g of the title compound.

$^1$H-NMR of the obtained compound are shown below:
$^1$H-NMR (CDCl$_3$) δ ppm: 0.11 (s, 3H), 0.29 (s, 3H), 0.88 (s, 9H), 2.88 (t, 5.4 Hz, 2H), 4.04 (t, 5.4 Hz, 2H), 7.25-7.50 (m, 8H), 7.65 (d, 7.7 Hz, 2H), 8.00 (s, 1H), 10.63 (brs, 1H)

Step 4

Synthesis of (E)-4-hydroxy-N-phenyl-2-(phenylthiomethylene)butanethioamide 1 ml of tetra n-butyl ammonium chloride (1 mol/l of tetrahydrofuran solution) was added to 5 ml of tetrahydrofuran solution including 0.4 g of (E)-4-(tert-butyldiphenylsilyloxy)-N-phenyl-2-(phenylthiomethylene)butanethioamide. The resulting solution was stirred at room temperature for 30 minutes and added with saturated ammonium chloride. The solution was extracted with ethyl acetate, dried with anhydrous magnesium sulfate and filtered, concentrated under reduced pressure. Crude (E)-4-hydroxy-N-phenyl-2-(phenylthiomethylene)butanethioamide was obtained. The crude was used in the next reaction without purification.

Step 5

Synthesis of (Z)—N-((E)-3-(phenylthiomethylene) dihydrothiophen-2(3H)-ylidene)aniline 0.13 g of methanesulfonyl chloride was added to 10 ml of methylene chloride suspension including 0.4 g of (E)-4-hydroxy-N-phenyl-2-(phenylthiomethylene)butanethioamide and 0.11 g of triethylamine. The resulting solution was stirred at room temperature for 2 hours, and added with water, extracted with ethyl acetate. The organic layer was washed with brine, and dried with anhydrous magnesium sulfate, filtered, and concentrated under reduced pressure. The residue was purified by silica gel column chromatography to obtain 0.05 g of (Z)—N-((E)-3-(phenylthiomethylene)dihydrothiophen-2(3H)-ylidene) aniline and 0.05 g of 1-phenyl-3-(1-(phenylthio)ethylidene)pyrrolidine-2-thione.

$^1$H-NMR and the physical properties of the obtained compound are shown below:

(Z)—N-((E)-3-(phenylthiomethylene)dihydrothiophen-2 (3H)-ylidene)aniline:

$^1$H-NMR (CDCl$_3$) δ ppm: 2.99 (dt, 2.0 Hz, 6.8 Hz, 2H), 3.21 (t, 6.8 Hz, 2H), 7.0 (d, 2H), 7.1 (t, 1H), 7.25-7.4 (m, 5H), 7.48-7.55 (m, 3H)

1-phenyl-3-(1-(phenylthio)ethylidene)pyrrolidine-2-thione:
m.p. (melting point) 110-112° C.

Example 2

Production of (Z)—N-((E)-3-(phenylthiomethylene) tetrahydro-2H-thiopyran-2-ylidene) aniline Step 1

Synthesis of (E)-(2-oxo-2H-pyran-3(4H, 5H, 6H)-ylidene)methyl methanesulfonate 20 ml of tetrahydrofuran solution including 2 g of valerolactone was cooled to 0° C. and added with 0.96 g of NaH (60%). The resulting solution was stirred for 5 minutes and added with 1.63 g of ethyl formate and 0.2 ml of ethanol. Then, the resulting solution was stirred at 0° C. for 1 hour, and the temperature was raised to room temperature. After stirring for one night, the solution was concentrated under reduced pressure. The residue was suspended by adding tetrahydrofuran and cooled to 0° C. The resulting solution was added with 2.52 g of methanesulfonyl chloride and stirred at 0° C. for 30 minutes, followed by stirring at room temperature for an additional 4 hours. The resulting solution was added with saturated sodium bicarbonate water, and extracted with ethyl acetate. The organic layer was washed with brine, dried with anhydrous magnesium sulfate, filtered, and concentrated under reduced pressure. Crude (E)-(2-oxo-2H-pyran-3(4H, 5H, 6H)-ylidene)methyl methanesulfonate was obtained. The crude was used in the next reaction without purification.

Step 2

Synthesis of (E)-3-(phenylthiomethylene)tetrahydro-2H-pyran-2-one 20 ml of N,N-dimethylformamide solution including 2.31 g of benzene thiol was cooled to 0° C. and added with 0.96 g of NaH (60%). The resulting solution was stirred for 20 minutes and added with 10 ml of N,N-dimethylformamide solution including the above descried crude. After stirring for 30 minutes, the temperature was raised to room temperature, and the solution was stirred for one night. The solution was added with saturated ammonium chloride aqueous solution and extracted with ethyl acetate. The organic layer was washed with water 3 times, then washed with brine, and dried with anhydrous magnesium sulfate, filtered, and concentrated under reduced pressure. The residue was purified by silica gel column chromatography to obtain 2.87 g of E-form, 0.33 g of Z-form.

$^1$H-NMR and the physical properties of the obtained compound are shown below:

E-form: nD22.9 1.5864;

$^1$H-NMR (CDCl$_3$) δ ppm: 2.02 (m, 2H), 2.55 (dt, 2H), 4.36 (t, 2H), 7.35-7.49 (m, 5H), 7.99 (t, 1H)

Z-form: m.p. (melting point) 141-142° C.;

$^1$H-NMR (CDCl$_3$) δ ppm: 1.95 (m, 2H), 2.65 (dt, 2H), 4.37 (t, 2H), 7.12 (t, 1H), 7.35-7.52 (m, 5H)

Step 3

Synthesis of (E)-5-hydroxy-N-phenyl-2-(phenylthiomethylene)pentanamide 6.4 ml of diethylalumiun chloride (1 mol/l of hexane solution) was added to 10 ml of methylene chloride solution including 0.6 g of aniline at room temperature. After stirring for 5 minutes, methylene chloride solution including 1.28 g of (E)-3-(phenylthiomethylene)tetrahydro-2H-pyran-2-one was dropped into the resulting solution. After stirring at room temperature for 2 hours, the solution was added with 10% hydrochloric acid, then stirred at room temperature for 30 minutes. The solution was extracted with ethyl acetate, and the organic layer was washed with brine, dried with anhydrous magnesium sulfate, filtered, and concentrated under reduced pressure. The residue was purified by silica gel column chromatography to obtain 1.64 g of the title compound.

$^1$H-NMR of the obtained compound is shown below:

$^1$H-NMR (CDCl$_3$) δ ppm: 1.93 (m, 2H), 2.70 (t, 2H), 3.76 (t, 2H), 6.97-7.60 (m, 11H), 8.40 (brs, 1H)

Step 4

Synthesis of (E)-5-(tert-butyldiphenylsilyloxy)-N-phenyl-2-(phenylthiomethylene) pentanamide 1.87 g of chloro t-butyl diphenylsilane was dropped into 10 ml of methylene chloride solution including 1.64 g of (E)-5-hydroxy-N-phenyl-2-(phenylthiomethylene)pentanamide and 0.82 g of imidazole at room temperature. After stirring at room temperature for 2 hours, the resulting solution was added with water and extracted with ethyl acetate. The organic layer was washed 3 times, then washed with brine, and dried with anhydrous magnesium sulfate, filtered, and concentrated under reduced pressure. The residue was purified by silica gel column chromatography to obtain 2.81 g the title compound.

$^1$H-NMR of the obtained compound is shown below:

$^1$H-NMR (CDCl$_3$) δ ppm: 1.09 (s, 9H), 1.84 (m, 2H), 2.70 (t, 2H), 3.81 (t, 2H), 7.10-7.73 (m, 21H)

Synthesis of (E)-5-(tert-butyldiphenylsilyloxy)-N-phenyl-2-(phenylthiomethylene) pentanethioamide Lawesson reagent was added to tetrahydrofuran solution including 2.81 g of (E)-5-(tert-butyldiphenylsilyloxy)-N-phenyl-2-(phenylthiomethylene)pentanamide. The resulting solution was heated under reflux for one night and cooled to room temperature, followed by adding saturated sodium bicarbonate water to extract. The water layer was extracted with ethyl acetate, and the organic layer was mixed and dried with anhydrous magnesium sulfate, then filtered, and concentrated under reduced pressure. The residue was purified by silica gel column chromatography to obtain 2.17 g of the title compound.

$^1$H-NMR of the obtained compound is shown below:

$^1$H-NMR (CDCl$_3$) δ ppm: 1.02 (s, 9H), 1.86 (m, 2H), 2.89 (t, 2H), 3.82 (t, 2H), 7.20-7.74 (m, 21H), 9.05 (brs, 1H)

Step 6

Synthesis of (E)-5-hydroxy-N-phenyl-2-(phenylthiomethylene)pentanethioamide 4 ml of tetra n-butyl ammonium chloride (1 mol/l of tetrahydrofuran solution) was added to 20 ml of tetrahydrofuran solution including 2.17 g of (E)-5-(tert-butykliphenylsilyloxy)-N-phenyl-2-(phenylthiomethylene)pentanethioamide. The resulting solution was stirred at room temperature for 30 minutes and added with saturated ammonium chloride. The solution was extracted with ethyl acetate, dried with anhydrous magnesium sulfate and filtered, concentrated under reduced pressure. Crude (E)-5-hydroxy-N-phenyl-2-(phenylthiomethylene)pentanethioamide was obtained. The crude was used in the next reaction without purification.

Step 7)

Synthesis of (Z)—N-((E)-3-(phenylthiomethylene)tetrahydro-2H-thiopyran-2-ylidene) aniline 0.48 g of methanesulfonyl chloride was added to 20 ml of methylene chloride solution including 0.4 g of (E)-5-hydroxy-N-phenyl-2-(phenylthiomethylene) pentanethioamide, 0.46 g of triethylamine and 0.69 of sodium iodide. The resulting solution was stirred at room temperature for 3 hours, and added with water, extracted with ethyl acetate. The organic layer was washed with brine, dried with anhydrous magnesium sulfate, filtered, and concentrated under reduced pressure. The residue was purified by silica gel column chromatography to obtain 0.23 g of the title compound.

¹H-NMR of the obtained compound is shown below:

m.p. (melting point) 79-81° C.;

¹H-NMR (CDCl₃) δ ppm: 2.15 (m, 2H), 2.68 (dt, 2.0 Hz, 6.8 Hz, 2H), 2.92 (t, 6.8 Hz, 2H), 6.8-7.6 (m, 11H)

Example 3

Production of (4-chloro-phenyl)-{3-[1-phenyl sulfanyl-(E)-methylidene]-3,4,4a,5,6,8a-hexahydro-thiochromene-(2Z)-ylidene}-amine

[Chemical formula 11]

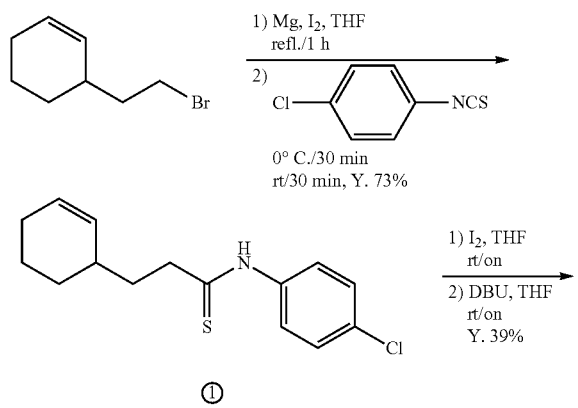

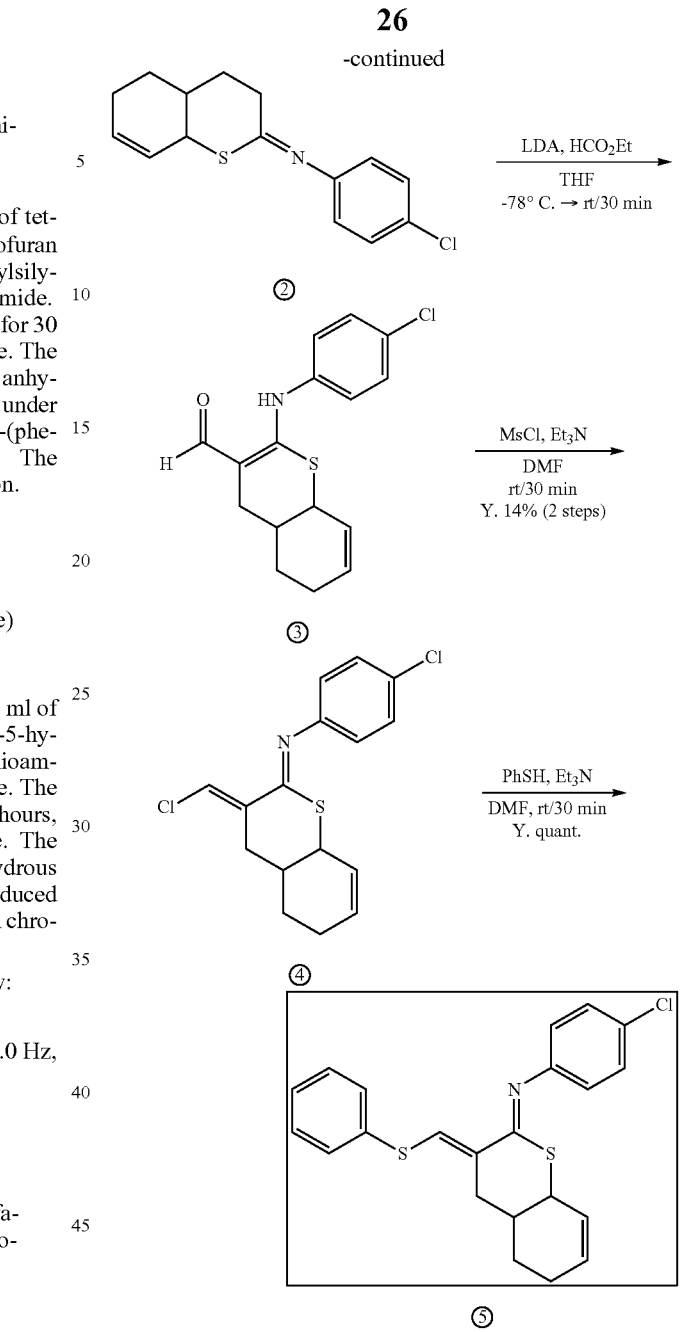

Step 1

Synthesis of N-(4-chlorophenyl)-3-(2-cyclohexene-1-yl)thiopropionamide 0.39 g of magnesium and a catalyst quantity of iodine were added to 25 ml of anhydrous tetrahydrofuran (anhydrous THF) solution, and 25 ml of tetrahydrofuran solution including 3.0 g of 3-(2-bromoethyl)cyclohexene was dropped into the resulting solution under reflux. The solution was stirred for one additional hour under reflux, and cooled to room temperature, thereby obtaining THF solution of 2-(2-cyclohexene-1-yl)ethyl magnesium bromide.

The obtained THF solution of 2-(2-cyclohexene-1-yl)ethyl magnesium bromide was dropped into 25 ml of anhydrous THF solution including 1.8 g of p-chlorophenyl isothiocyanate at 0° C. The resulting solution was stirred at 0° C. for 30 minutes, and stirred at room temperature for an additional 30 minutes. The solution was added with saturated ammonium chloride aqueous solution and extracted with ethyl acetate. The organic layer was washed with brine, dried with anhydrous magnesium sulfate, filtered, concentrated under reduced pressure. The residue was purified by silica gel column chromatography to obtain 2.2 g of the title compound.

$^1$H-NMR of the obtained compound is shown below:
$^1$H-NMR (CDCl$_3$) δ ppm:
1.29 (m, 1H), 1.51-2.05 (m, 7H), 2.21 (m, 1H), 2.85 (t, 2H), 5.59 (d, 1H), 5.73 (m, 1H), 7.37 (d, 2H), 7.62 (d, 2H), 8.59 (brs, 1H)

Step 2

Synthesis of (4-chlorophenyl)-(3,4,4a,5,6,8a-hexahydro-thiochromene-2-ylidene)-amine 10 ml of THF solution including 2.4 g of iodine was added to 40 ml of THF solution including 2.2 g of N-(4-chlorophenyl)-3-(2-cyclohexene-1-yl) thiopropionamide at 0° C. The temperature was raised to room temperature and the resulting solution was stirred for one night. Then the temperature was cooled to 0° C., and 5 ml of THF solution including 4.1 g of 1,4 diazabicyclo[5,4,0]undec-7-ene(DBU) was dropped into the resulting solution. The solution was stirred at room temperature for one night, and added with water, and extracted with ethyl acetate. The organic layer was washed with brine, dried with anhydrous magnesium sulfate, filtered, and concentrated under reduced pressure. The residue was purified by silica gel column chromatography to obtain 0.84 of the title compound.

$^1$H-NMR of the obtained compound is shown below:
$^1$H-NMR (CDCl$_3$) δ ppm:
1.48 (m, 1H), 1.65 (m, 2H), 2.10 (m, 2H), 2.25 (m, 2H), 2.74 (m, 2H), 3.99 (brs, 1H), 5.57 (m, 1H), 5.90 (m, 1H), 6.81 (d, 2H), 7.28 (d, 2H)

Step 3

Synthesis of {3-[1-chloro-(E)-methylidene]-3,4,4a,5,6,8a-hexahydro-thiochromene-(2Z)-ylidene}-(4-chloro-phenyl)-amine 3.0 ml of lithium diisopropyl amide (1.5 mol/l of THF/cyclohexane solution) was dropped into 20 ml of anhydrous THF solution including 0.84 g of (4-chlorophenyl)-(3,4,4a,5,6,8a-hexahydro-thiochromene-2-ylidene)-amine under nitrogen atmosphere at −78° C. After stirring at −78° C. for 30 minutes, 2 ml of THF solution including 0.34 g of ethyl formate was dropped into the resulting solution. The solution was stirred at room temperature for one additional hour, and added with saturated ammonium chloride aqueous solution, extracted with ethyl acetate. The organic layer was washed with brine, dried with anhydrous magnesium sulfate, filtered, and concentrated under reduced pressure to obtain crude 2-(4-chloro-phenylamino)-4a,5,6,8a-tetrahydro-4H-thiochromene-3-carbaldehyde.

0.46 g of triethylamine and 0.52 g of methanesulfonyl chloride were added to 10 ml of dimethylformamide (DMF) solution including the above obtained crude at 0° C. The solution was stirred at room temperature for one additional hour, and added with water, extracted with ethyl acetate. The organic layer was washed with brine, and dried with anhydrous magnesium sulfate, filtered, and concentrated under reduced pressure. The residue was purified by silica gel column chromatography to obtain 0.14 g of the title compound.

Step 4

Synthesis of (4-chloro-phenyl)-{3-[1-phenyl sulfanyl-(E)-methylidene]-3,4,4a,5,6,8a-hexahydro-thiochromene-(2Z)-ylidene}-amine 65 mg of trimethylamine and 1 ml of DMF solution including {3-[1-chloro-(E)-methylidene]-3,4,4a,5,6,8a-hexahydro-thiochromene-(2Z)-ylidene}-(4-chloro-phenyl)-amine were added to 2 ml of DMF solution including 47 mg of thiophenol at 0° C. The resulting solution was stirred at room temperature for an additional 30 minutes, and added with water, and then extracted with ethyl acetate. The organic layer was washed with brine, dried with anhydrous magnesium sulfate, filtered, and concentrated under reduced pressure. The residue was purified by silica gel column chromatography to obtain 0.17 g of the title compound.

$^1$H-NMR of the obtained compound is shown below:
$^1$H-NMR (CDCl$_3$) δ ppm:
1.75-1.80 (m, 2H), 2.14-2.17 (m, 2H), 2.29 (q, 1H), 2.26-2.33 (m, 1H), 3.25 (q, 1H), 3.87 (brs, 1H), 5.56-5.61 (m, 1H), 5.89-5.92 (m, 1H), 6.84 (d, 2H), 7.25-7.39 (m, 6H), 7.49 (d, 2H)

The compounds of the present invention including the Examples, that are obtained by the above-described production methods are shown in the following tables. In the physical properties, "vis" indicates viscous oil, "amor" indicates amorphous. In addition, "nD22.9-1.6037" indicates that the refraction index is 1.6037 at 22.9° C. "m.p." indicates the melting point. The compounds represented by formula (1) are shown in TABLES 1-1 to 1-3, the compounds represented by formula (II) are shown in TABLES 2-1 to 2-3, the compounds represented by formula (III) were shown the TABLES 3-1 to 3-4, and the compounds represented by formula (IV) were shown TABLES 4-1 to 4-4.

In addition, the abbreviations described in the tables have the meanings as defined below:

Me: Methyl group, iPr: isopropyl group, Ph: phenyl group,

Py-2-yl: pyridine-2-yl group, cHex: cyclohenxane, Bn: benzyl group

In the tables, if $(R^1)_m$, $(R^2)_p$ and $(R^3)$, are represented by "-", it means that it is not substituted by $R^1$, $R^2$ or $R^3$, namely, m, p and r represents 0.

In addition, TABLES 1-1 to 4-4 only show some of the compounds of the present invention. The ordinary skilled person can easily understand that other compounds which are not shown in this description, namely, the compounds which are substituted by various substituents complying with the purpose and scope of the present invention can also be obtained by the above-described method and can be used.

[Chemical formula 12]

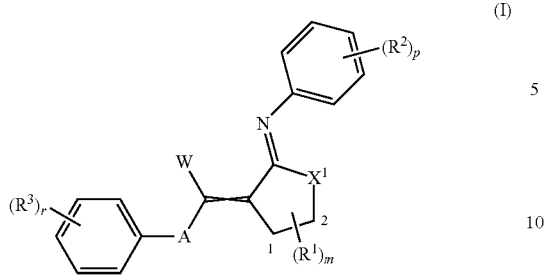

(I)

TABLE 1

TABLE 1-1

| Compound | $(R^1)_m$ | $(R^2)_p$ | $(R^3)_r$ | $X^1$ | W | A | E/Z | Physical property |
|---|---|---|---|---|---|---|---|---|
| 1a-1 | — | — | — | S | H | S | E | Viscous oil |
| 1a-2 | — | 2-Me | — | S | H | S | E | Viscous oil |
| 1a-3 | — | 3-Me | — | S | H | S | E | Viscous oil |
| 1a-4 | — | 4-Me | — | S | H | S | E | Viscous oil |
| 1a-5 | — | 4-iPr | — | S | H | S | E | Viscous oil |
| 1a-6 | — | 4-OH | — | S | H | S | E | |
| 1a-7 | — | 4-OMe | — | S | H | S | E | |
| 1a-8 | — | 4-NH$_2$ | — | S | H | S | E | |
| 1a-9 | — | 4-NMe$_2$ | — | S | H | S | E | |
| 1a-10 | — | 4-F | — | S | H | S | E | |
| 1a-11 | — | 4-Cl | — | S | H | S | E | |
| 1a-12 | — | 2,6-Cl$_2$ | — | S | H | S | E | |
| 1a-13 | — | 4-CF$_3$ | — | S | H | S | E | |
| 1a-14 | — | 4-CN | — | S | H | S | E | |
| 1a-15 | — | 4-NO$_2$ | — | S | H | S | E | |
| 1a-16 | — | 4-Ph | — | S | H | S | E | |
| 1a-17 | — | 4-(Py-2-yl) | — | S | H | S | E | |
| 1a-18 | — | 4-CO$_2$Me | — | S | H | S | E | |
| 1a-19 | — | 4-SO$_2$Me | — | S | H | S | E | |
| 1a-20 | — | — | 4-Me | S | H | S | E | |
| 1a-21 | — | — | 4-OMe | S | H | S | E | |
| 1a-22 | — | — | 4-F | S | H | S | E | |
| 1a-23 | — | — | 4-Cl | S | H | S | E | |
| 1a-24 | — | — | 2,6-Cl$_2$ | S | H | S | E | |
| 1a-25 | 1-Me | — | — | S | H | S | E | |
| 1a-26 | 2-Me | — | — | S | H | S | E | |
| 1a-27 | 2-Me$_2$ | — | — | S | H | S | E | |
| 1a-28 | 1-F | — | — | S | H | S | E | |
| 1a-29 | 2-F | — | — | S | H | S | E | |
| 1a-30 | 1,1,2,2-F$_4$ | — | — | S | H | S | E | |
| 1a-31 | — | 4-Me | 4-Me | S | H | S | E | Viscous oil |
| 1a-32 | — | 4-Me | 4-F | S | H | S | E | Viscous oil |
| 1a-33 | 2-Me | 4-Me | — | S | H | S | E | Viscous oil |
| 1a-34 | — | — | — | O | H | S | E | Viscous oil |
| 1a-35 | — | 4-Me | — | O | H | S | E | nD22.8-1.6532 |
| 1a-36 | — | 4-OMe | — | O | H | S | E | |
| 1a-37 | — | 4-Cl | — | O | H | S | E | |
| 1a-38 | — | 2,6-Cl$_2$ | — | O | H | S | E | |
| 1a-39 | — | — | 4-Me | O | H | S | E | |
| 1a-40 | — | — | 4-OMe | O | H | S | E | |

TABLE 2

TABLE 1-2

| Compound | $(R^1)_m$ | $(R^2)_p$ | $(R^3)_r$ | $X^1$ | W | A | E/Z | Physical property |
|---|---|---|---|---|---|---|---|---|
| 1a-41 | — | — | 4-Cl | O | H | S | E | |
| 1a-42 | — | — | 2,6-Cl$_2$ | O | H | S | E | |

TABLE 2-continued

TABLE 1-2

| Compound | $(R^1)_m$ | $(R^2)_p$ | $(R^3)_r$ | $X^1$ | W | A | E/Z | Physical property |
|---|---|---|---|---|---|---|---|---|
| 1a-43 | — | — | — | S | H | O | E | |
| 1a-44 | — | 4-Me | — | S | H | O | E | |
| 1a-45 | — | 4-OMe | — | S | H | O | E | |
| 1a-46 | — | 4-Cl | — | S | H | O | E | |
| 1a-47 | — | 2,6-Cl$_2$ | — | S | H | O | E | |
| 1a-48 | — | — | 4-Me | S | H | O | E | |
| 1a-49 | — | — | 4-OMe | S | H | O | E | |
| 1a-50 | — | — | 4-Cl | S | H | O | E | |
| 1a-51 | — | — | 2,6-Cl$_2$ | S | H | O | E | |
| 1a-52 | — | — | — | O | H | O | E | |
| 1a-53 | — | 4-Me | — | O | H | O | E | |
| 1a-54 | — | 4-OMe | — | O | H | O | E | |
| 1a-55 | — | 4-Cl | — | O | H | O | E | |
| 1a-56 | — | 2,6-Cl$_2$ | — | O | H | O | E | |
| 1a-57 | — | — | 4-Me | O | H | O | E | |
| 1a-58 | — | — | 4-OMe | O | H | O | E | |
| 1a-59 | — | — | 4-Cl | O | H | O | E | |
| 1a-60 | — | — | 2,6-Cl$_2$ | O | H | O | E | |
| 1a-61 | — | — | — | O | H | SO$_2$ | E | |
| 1a-62 | — | 4-Me | — | O | H | SO$_2$ | E | |
| 1a-63 | — | 4-OMe | — | O | H | SO$_2$ | E | |
| 1a-64 | — | 4-Cl | — | O | H | SO$_2$ | E | |
| 1a-65 | — | 2,6-Cl$_2$ | — | O | H | SO$_2$ | E | |
| 1a-66 | — | — | 4-Me | O | H | SO$_2$ | E | |
| 1a-67 | — | — | 4-OMe | O | H | SO$_2$ | E | |
| 1a-68 | — | — | 4-Cl | O | H | SO$_2$ | E | |
| 1a-69 | — | — | 2,6-Cl$_2$ | O | H | SO$_2$ | E | |
| 1a-70 | — | — | — | S | Me | S | E | |
| 1a-71 | — | 4-Me | — | S | Me | S | E | m.p. 77-79 |
| 1a-72 | — | 4-OMe | — | S | Me | S | E | |
| 1a-73 | — | 4-Cl | — | S | Me | S | E | |
| 1a-74 | — | 2,6-Cl$_2$ | — | S | Me | S | E | |
| 1a-75 | — | — | — | S | CF$_3$ | S | E | |
| 1a-76 | — | 4-Me | — | S | CF$_3$ | S | E | |
| 1a-77 | — | 4-OMe | — | S | CF$_3$ | S | E | |
| 1a-78 | — | 4-Cl | — | S | CF$_3$ | S | E | |
| 1a-79 | — | 2,6-Cl$_2$ | — | S | CF$_3$ | S | E | |

TABLE 3

TABLE 1-2

| Compound | $(R^1)_m$ | $(R^2)_p$ | $(R^3)_r$ | $X^1$ | W | A | E/Z | Physical property |
|---|---|---|---|---|---|---|---|---|
| 1a-80 | 2-Me | 4-Me | — | O | H | S | E | nD22.7-1.6312 |
| 1a-81 | 1-Me | 4-Me | — | S | H | S | E | |
| 1a-82 | — | 4-Me | 3-F | S | H | S | E | nD23.1-1.6601 |
| 1a-83 | — | 4-Me | — | O | Me | S | E | nD22.5-1.6482 |
| 1a-84 | 2-(CH$_2$)$_2$CH$_3$ | 4-Me | — | O | H | S | E | nD22.5-1.6298 |
| 1a-85 | 2-Ph | 4-Me | — | O | H | S | E | nD21.9-1.6583 |
| 1a-86 | 2,2-Me$_2$ | 4-Me | — | O | H | S | E | m.p. 102-103 |

TABLE 4

TABLE 1-3

| Compound | $(R^1)_m$ | $(R^2)_p$ | $(R^3)_r$ | $X^1$ | W | A | E/Z | Physical property |
|---|---|---|---|---|---|---|---|---|
| 1b-1 | — | — | — | S | H | S | Z | |
| 1b-2 | — | 4-Me | — | S | H | S | Z | |
| 1b-3 | — | 4-OMe | — | S | H | S | Z | |
| 1b-4 | — | 4-F | — | S | H | S | Z | |
| 1b-5 | — | 4-Cl | — | S | H | S | Z | |
| 1b-6 | — | 2,6-Cl$_2$ | — | S | H | S | Z | |
| 1b-7 | — | — | 4-Me | S | H | S | Z | |
| 1b-8 | — | — | 4-OMe | S | H | S | Z | |
| 1b-9 | — | — | 4-F | S | H | S | Z | |
| 1b-10 | — | — | 4-Cl | S | H | S | Z | |
| 1b-11 | — | — | 2,6-Cl$_2$ | S | H | S | Z | |
| 1b-12 | 1-Me | — | — | S | H | S | Z | |
| 1b-13 | 2-Me | — | — | S | H | S | Z | |
| 1b-14 | 1-F | — | — | S | H | S | Z | |
| 1b-15 | 2-F | — | — | S | H | S | Z | |
| 1b-16 | — | — | — | O | H | S | Z | |
| 1b-17 | — | 4-Me | — | O | H | S | Z | |
| 1b-18 | — | 4-OMe | — | O | H | S | Z | |

TABLE 4-continued

TABLE 1-3

| Compound | $(R^1)_m$ | $(R^2)_p$ | $(R^3)_r$ | $X^1$ | W | A | E/Z | Physical property |
|---|---|---|---|---|---|---|---|---|
| 1b-19 | — | 4-Cl | — | O | H | S | Z | |
| 1b-20 | — | 2,6-Cl$_2$ | — | O | H | S | Z | |
| 1b-21 | — | — | — | S | H | O | Z | |
| 1b-22 | — | 4-Me | — | S | H | O | Z | |
| 1b-23 | — | 4-OMe | — | S | H | O | Z | |
| 1b-24 | — | 4-Cl | — | S | H | O | Z | |
| 1b-25 | — | 2,6-Cl$_2$ | — | S | H | O | Z | |
| 1b-26 | — | — | — | O | H | S | Z | |
| 1b-27 | — | 4-Me | — | O | H | S | Z | |
| 1b-28 | — | 4-OMe | — | O | H | S | Z | |
| 1b-29 | — | 4-Cl | — | O | H | S | Z | |
| 1b-30 | — | 2,6-Cl$_2$ | — | O | H | S | Z | |
| 1b-31 | — | — | — | O | H | O | Z | |
| 1b-32 | — | 4-Me | — | O | H | O | Z | |
| 1b-33 | — | 4-OMe | — | O | H | O | Z | |
| 1b-34 | — | 4-Cl | — | O | H | O | Z | |
| 1b-35 | — | 2,6-Cl$_2$ | — | O | H | O | Z | |

TABLE 5

TABLE 1-3

| Compound | $(R^1)_m$ | $(R^2)_p$ | $(R^3)_r$ | $X^1$ | W | A | E/Z | Physical property |
|---|---|---|---|---|---|---|---|---|
| 1b-36 | — | 4-Me | — | S | Me | S | Z | m.p. 115-117 |

[Chemical formula 13]

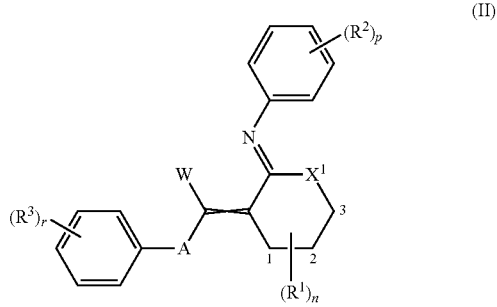

(II)

TABLE 6

TABLE 2-1

| Compound | $(R^1)_m$ | $(R^2)_p$ | $(R^3)_r$ | $X^1$ | W | A | E/Z | Physical property |
|---|---|---|---|---|---|---|---|---|
| 2a-1 | — | — | — | S | H | S | E | m.p. 79-81° C. |
| 2a-2 | — | 2-Me | — | S | H | S | E | |
| 2a-3 | — | 3-Me | — | S | H | S | E | |
| 2a-4 | — | 4-Me | — | S | H | S | E | m.p. 80-82° C. |
| 2a-5 | — | 4-iPr | — | S | H | S | E | |
| 2a-6 | — | 4-OH | — | S | H | S | E | |
| 2a-7 | — | 4-OMe | — | S | H | S | E | m.p. 95-97° C. |
| 2a-8 | — | 4-NH$_2$ | — | S | H | S | E | |
| 2a-9 | — | 4-NMe$_2$ | — | S | H | S | E | |
| 2a-10 | — | 4-F | — | S | H | S | E | |
| 2a-11 | — | 4-Cl | — | S | H | S | E | |
| 2a-12 | — | 2,6-Cl$_2$ | — | S | H | S | E | |
| 2a-13 | — | 4-CF$_3$ | — | S | H | S | E | |
| 2a-14 | — | 4-CN | — | S | H | S | E | |
| 2a-15 | — | 4-NO$_2$ | — | S | H | S | E | |
| 2a-16 | — | 4-Ph | — | S | H | S | E | |
| 2a-17 | — | 4-(Py-2-yl) | — | S | H | S | E | |
| 2a-18 | — | 4-CO$_2$Me | — | S | H | S | E | |
| 2a-19 | — | 4-SO$_2$Me | — | S | H | S | E | |
| 2a-20 | — | — | 4-Me | S | H | S | E | |
| 2a-21 | — | — | 4-OMe | S | H | S | E | |
| 2a-22 | — | — | 4-F | S | H | S | E | |
| 2a-23 | — | — | 4-Cl | S | H | S | E | |
| 2a-24 | — | — | 2,6-Cl$_2$ | S | H | S | E | |
| 2a-25 | 1-Me | — | — | S | H | S | E | |
| 2a-26 | 2-Me | — | — | S | H | S | E | |
| 2a-27 | 3-Me | — | — | S | H | S | E | |
| 2a-28 | 1-F | — | — | S | H | S | E | |
| 2a-29 | 2-F | — | — | S | H | S | E | |
| 2a-30 | 3-F | — | — | S | H | S | E | |
| 2a-31 | 1,1,2,2,3,3-F$_6$ | — | — | S | H | S | E | |
| 2a-32 | — | — | — | O | H | S | E | Viscous oil |

TABLE 6-continued

TABLE 2-1

| Compound | $(R^1)_m$ | $(R^2)_p$ | $(R^3)_r$ | $X^1$ | W | A | E/Z | Physical property |
|---|---|---|---|---|---|---|---|---|
| 2a-33 | — | 4-Me | — | O | H | S | E | |
| 2a-34 | — | 4-OMe | — | O | H | S | E | Viscous oil |
| 2a-35 | — | 4-Cl | — | O | H | S | E | |
| 2a-36 | — | 2,6-Cl$_2$ | — | O | H | S | E | |
| 2a-37 | — | — | 4-Me | O | H | S | E | |
| 2a-38 | — | — | 4-OMe | O | H | S | E | |
| 2a-39 | — | — | 4-Cl | O | H | S | E | |
| 2a-40 | — | — | 2,6-Cl$_2$ | O | H | S | E | |

TABLE 7

TABLE 2-2

| Compound | $(R^1)_m$ | $(R^2)_p$ | $(R^3)_r$ | $X^1$ | W | A | E/Z | Physical property |
|---|---|---|---|---|---|---|---|---|
| 2a-41 | — | — | — | S | H | O | E | |
| 2a-42 | — | 4-Me | — | S | H | O | E | |
| 2a-43 | — | 4-OMe | — | S | H | O | E | |
| 2a-44 | — | 4-Cl | — | S | H | O | E | |
| 2a-45 | — | 2,6-Cl$_2$ | — | S | H | O | E | |
| 2a-46 | — | — | 4-Me | S | H | O | E | |
| 2a-47 | — | — | 4-OMe | S | H | O | E | |
| 2a-48 | — | — | 4-Cl | S | H | O | E | |
| 2a-49 | — | — | 2,6-Cl$_2$ | S | H | O | E | |
| 2a-50 | — | — | — | O | H | O | E | |
| 2a-51 | — | 4-Me | — | O | H | O | E | |
| 2a-52 | — | 4-OMe | — | O | H | O | E | |

TABLE 7-continued

TABLE 2-2

| Compound | $(R^1)_m$ | $(R^2)_p$ | $(R^3)_r$ | $X^1$ | W | A | E/Z | Physical property |
|---|---|---|---|---|---|---|---|---|
| 2a-65 | — | — | 4-OMe | O | H | SO$_2$ | E | |
| 2a-66 | — | — | 4-Cl | O | H | SO$_2$ | E | |
| 2a-67 | — | — | 2,6-Cl$_2$ | O | H | SO$_2$ | E | |
| 2a-68 | — | — | — | S | Me | S | E | |
| 2a-69 | — | 4-Me | — | S | Me | S | E | |
| 2a-70 | — | 4-OMe | — | S | Me | S | E | |
| 2a-71 | — | 4-Cl | — | S | Me | S | E | |
| 2a-72 | — | 2,6-Cl$_2$ | — | S | Me | S | E | |
| 2a-73 | — | — | — | S | CF$_3$ | S | E | |
| 2a-74 | — | 4-Me | — | S | CF$_3$ | S | E | |
| 2a-75 | — | 4-OMe | — | S | CF$_3$ | S | E | |
| 2a-76 | — | 4-Cl | — | S | CF$_3$ | S | E | |
| 2a-77 | — | 2,6-Cl$_2$ | — | S | CF$_3$ | S | E | |

TABLE 8

TABLE 2-2

| Compound | $(R^1)_m$ | $(R^2)_p$ | $(R^3)_r$ | $X^1$ | W | A | E/Z | Physical property |
|---|---|---|---|---|---|---|---|---|
| 2a-78 | — | 4-Me | 4-F | S | H | S | E | Viscous oil |
| 2a-79 | — | 4-Cl | — | O | H | S | E | nD22.8-1.6417 |
| 2a-80 | — | 4-Cl | — | S | H | S | E | Amorphous |
| 2a-81 | — | 4-Me | — | O | H | S | E | nD22.6-1.6532 |
| 2a-82 | — | 3,4-Me2 | — | O | H | S | E | nD22.7-1.6428 |
| 2a-83 | 3-Me | 4-Me | — | O | H | S | E | nD21.8-1.6278 |
| 2a-84 | 3-(CH$_2$)$_2$CH$_3$ | 4-Me | — | O | H | S | E | nD22.0-1.6291 |
| 2a-85 | 3,3-Me$_2$ | 4-Me | — | O | H | S | E | m.p. 88-89° C. |
| 2a-86 | 3-Ph | 4-Me | — | O | H | S | E | m.p. 100-102 |
| 2a-87 | 3-Ph | 4-Me | — | S | H | S | E | m.p. 126-128° C. |
| 2a-88 | 3-Me | 4-Me | — | S | H | S | E | |
| 2a-89 | 3-iPr | 4-Me | — | S | H | S | E | |
| 2a-90 | 3,3-Me$_2$ | 4-Me | — | S | H | S | E | |
| 2a-91 | 2,2-Me$_2$ | 4-Me | — | S | H | S | E | |

TABLE 7-continued

TABLE 2-2

| Compound | $(R^1)_m$ | $(R^2)_p$ | $(R^3)_r$ | $X^1$ | W | A | E/Z | Physical property |
|---|---|---|---|---|---|---|---|---|
| 2a-53 | — | 4-Cl | — | O | H | O | E | |
| 2a-54 | — | 2,6-Cl$_2$ | — | O | H | O | E | |
| 2a-55 | — | — | 4-Me | O | H | O | E | |
| 2a-56 | — | — | 4-OMe | O | H | O | E | |
| 2a-57 | — | — | 4-Cl | O | H | O | E | |
| 2a-58 | — | — | 2,6-Cl$_2$ | O | H | O | E | |
| 2a-59 | — | — | — | O | H | SO$_2$ | E | |
| 2a-60 | — | 4-Me | — | O | H | SO$_2$ | E | |
| 2a-61 | — | 4-OMe | — | O | H | SO$_2$ | E | |
| 2a-62 | — | 4-Cl | — | O | H | SO$_2$ | E | |
| 2a-63 | — | 2,6-Cl$_2$ | — | O | H | SO$_2$ | E | |
| 2a-64 | — | — | 4-Me | O | H | SO$_2$ | E | |

TABLE 9

TABLE 2-3

| Compound | $(R^1)_m$ | $(R^2)_p$ | $(R^3)_r$ | $X^1$ | W | A | E/Z | Physical property |
|---|---|---|---|---|---|---|---|---|
| 2b-1 | — | — | — | S | H | S | Z | |
| 2b-2 | — | 4-Me | — | S | H | S | Z | |
| 2b-3 | — | 4-OMe | — | S | H | S | Z | |
| 2b-4 | — | 4-Cl | — | S | H | S | Z | |
| 2b-5 | — | 2,6-Cl$_2$ | — | S | H | S | Z | |
| 2b-6 | — | — | 4-Me | S | H | S | Z | |
| 2b-7 | — | — | 4-OMe | S | H | S | Z | |
| 2b-8 | — | — | 4-Cl | S | H | S | Z | |
| 2b-9 | — | — | 2,6-Cl$_2$ | S | H | S | Z | |
| 2b-10 | 1-Me | — | — | S | H | S | Z | |
| 2b-11 | 2-Me | — | — | S | H | S | Z | |
| 2b-12 | 3-Me | — | — | S | H | S | Z | |

TABLE 9-continued

TABLE 2-3

| Compound | $(R^1)_m$ | $(R^2)_p$ | $(R^3)_r$ | $X^1$ | W | A | E/Z | Physical property |
|---|---|---|---|---|---|---|---|---|
| 2b-13 | 1-F | — | — | S | H | S | Z | |
| 2b-14 | 2-F | — | — | S | H | S | Z | |
| 2b-15 | 3-F | — | — | S | H | S | Z | |
| 2b-16 | — | — | — | O | H | S | Z | |
| 2b-17 | — | 4-Me | — | O | H | S | Z | |
| 2b-18 | — | 4-OMe | — | O | H | S | Z | |
| 2b-19 | — | 4-Cl | — | O | H | S | Z | |
| 2b-20 | — | 2,6-Cl$_2$ | — | O | H | S | Z | |
| 2b-21 | — | — | — | S | H | O | Z | |
| 2b-22 | — | 4-Me | — | S | H | O | Z | |
| 2b-23 | — | 4-OMe | — | S | H | O | Z | |
| 2b-24 | — | 4-Cl | — | S | H | O | Z | |
| 2b-25 | — | 2,6-Cl$_2$ | — | S | H | O | Z | |
| 2b-26 | — | — | — | O | H | S | Z | |
| 2b-27 | — | 4-Me | — | O | H | S | Z | |
| 2b-28 | — | 4-OMe | — | O | H | S | Z | |
| 2b-29 | — | 4-Cl | — | O | H | S | Z | |
| 2b-30 | — | 2,6-Cl$_2$ | — | O | H | S | Z | |
| 2b-31 | — | — | — | O | H | O | Z | |
| 2b-32 | — | 4-Me | — | O | H | O | Z | |
| 2b-33 | — | 4-OMe | — | O | H | O | Z | |
| 2b-34 | — | 4-Cl | — | O | H | O | Z | |
| 2b-35 | — | 2,6-Cl$_2$ | — | O | H | O | Z | |

TABLE 10

TABLE 2-3

| Compound | $(R^1)m$ | $(R^2)p$ | $(R^3)r$ | $X^1$ | W | A | E/Z | Physical property |
|---|---|---|---|---|---|---|---|---|
| 2b-36 | — | 4-Me | 4-F | S | H | S | Z | Viscous oil |

[Chemical formula 14]

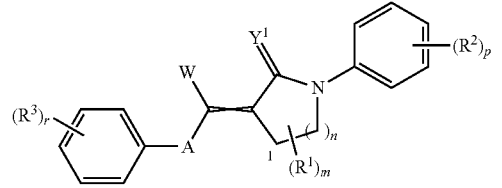

(III)

TABLE 11

TABLE 3-1

| Compound | $(R^1)_m$ | $(R^2)_p$ | $(R^3)_r$ | $Y^1$ | W | A | n | E/Z | Physical property |
|---|---|---|---|---|---|---|---|---|---|
| 3a-1 | — | — | — | S | H | S | 1 | E | m.p. 110-112° C. |
| 3a-2 | — | 2-Me | — | S | H | S | 1 | E | Viscous oil |
| 3a-3 | — | 3-Me | — | S | H | S | 1 | E | |
| 3a-4 | — | 4-Me | — | S | H | S | 1 | E | |
| 3a-5 | — | 4-iPr | — | S | H | S | 1 | E | m.p. 98-100° C. |
| 3a-6 | — | 4-OH | — | S | H | S | 1 | E | |
| 3a-7 | — | 4-OMe | — | S | H | S | 1 | E | |
| 3a-8 | — | 4-NH$_2$ | — | S | H | S | 1 | E | |
| 3a-9 | — | 4-NMe$_2$ | — | S | H | S | 1 | E | |
| 3a-10 | — | 4-F | — | S | H | S | 2 | E | |
| 3a-11 | — | 4-Cl | — | S | H | S | 1 | E | |
| 3a-12 | — | 2,6-Cl$_2$ | — | S | H | S | 1 | E | |
| 3a-13 | — | 4-CF$_3$ | — | S | H | S | 1 | E | |
| 3a-14 | — | 4-CN | — | S | H | S | 1 | E | |
| 3a-15 | — | 4-NO$_2$ | — | S | H | S | 1 | E | |
| 3a-16 | — | 4-Ph | — | S | H | S | 1 | E | |
| 3a-17 | — | 4-(Py-2-yl) | — | S | H | S | 1 | E | |
| 3a-18 | — | 4-CO$_2$Me | — | S | H | S | 1 | E | |
| 3a-19 | — | 4-SO$_2$Me | — | S | H | S | 1 | E | |
| 3a-20 | — | — | 4-Me | S | H | S | 1 | E | |
| 3a-21 | — | — | 4-OMe | S | H | S | 1 | E | |
| 3a-22 | — | — | 4-F | S | H | S | 2 | E | |
| 3a-23 | — | — | 4-Cl | S | H | S | 1 | E | |
| 3a-24 | — | — | 2,6-Cl$_2$ | S | H | S | 1 | E | |
| 3a-25 | — | 4-Me | 4-Me | S | H | S | 1 | E | m.p. 117-118° C. |
| 3a-26 | — | 4-Me | 4-F | S | H | S | 1 | E | m.p. 124-125° C. |

TABLE 11-continued

TABLE 3-1

| Compound | $(R^1)_m$ | $(R^2)_p$ | $(R^3)_r$ | $Y^1$ | W | A | n | E/Z | Physical property |
|---|---|---|---|---|---|---|---|---|---|
| 3a-27 | 2-Me | 4-Me | — | S | H | S | 1 | E | |
| 3a-28 | 2-Me$_2$ | 4-Me | — | S | H | S | 1 | E | |
| 3a-29 | 1,1,2,2-F$_4$ | 4-Me | — | S | H | S | 1 | E | |
| 3a-30 | — | — | — | O | H | S | 1 | E | m.p. 115-116° C. |
| 3a-31 | — | 4-Me | — | O | H | S | 1 | E | m.p. 118-119° C. |
| 3a-32 | — | 4-OMe | — | O | H | S | 1 | E | |
| 3a-33 | — | 4-Cl | — | O | H | S | 1 | E | |
| 3a-34 | — | 2,6-Cl$_2$ | — | O | H | S | 1 | E | |
| 3a-35 | — | — | 4-Me | O | H | S | 1 | E | |
| 3a-36 | — | — | 4-OMe | O | H | S | 1 | E | |
| 3a-37 | — | — | 4-Cl | O | H | S | 1 | E | |
| 3a-38 | — | — | 2,6-Cl$_2$ | O | H | S | 1 | E | |
| 3a-39 | — | — | — | O | H | S | 1 | E | |
| 3a-40 | — | 4-Me | — | O | H | S | 1 | E | |

TABLE 12

TABLE 3-2

| Compound | $(R^1)_m$ | $(R^2)_p$ | $(R^3)_r$ | $Y^1$ | W | A | n | E/Z | Physical property |
|---|---|---|---|---|---|---|---|---|---|
| 3a-41 | — | 4-OMe | — | O | H | S | 1 | E | |
| 3a-42 | — | 4-Cl | — | O | H | S | 1 | E | |
| 3a-43 | — | 2,6-Cl$_2$ | — | O | H | S | 1 | E | |
| 3a-44 | — | — | 4-Me | O | H | S | 1 | E | |
| 3a-45 | — | — | 4-OMe | O | H | S | 1 | E | |
| 3a-46 | — | — | 4-Cl | O | H | S | 1 | E | |
| 3a-47 | — | — | 2,6-Cl$_2$ | O | H | S | 1 | E | |
| 3a-48 | — | — | — | S | Me | S | 1 | E | |
| 3a-49 | — | 4-Me | — | S | Me | S | 1 | E | |
| 3a-50 | — | 4-OMe | — | S | Me | S | 1 | E | |
| 3a-51 | — | 4-Cl | — | S | Me | S | 1 | E | |
| 3a-52 | — | 2,6-Cl$_2$ | — | S | Me | S | 1 | E | |
| 3a-53 | — | — | — | S | CF$_3$ | S | 1 | E | |
| 3a-54 | — | 4-Me | — | S | CF$_3$ | S | 1 | E | |
| 3a-55 | — | 4-OMe | — | S | CF$_3$ | S | 1 | E | |
| 3a-56 | — | 4-Cl | — | S | CF$_3$ | S | 1 | E | |
| 3a-57 | — | 2,6-Cl$_2$ | — | S | CF$_3$ | S | 1 | E | |

TABLE 13

TABLE 3-2

| Compound | (R$^1$)m | (R$^2$)p | (R$^3$)r | $Y^1$ | W | A | n | E/Z | Physical property |
|---|---|---|---|---|---|---|---|---|---|
| 3a-58 | — | 4-Me | 2-F | S | H | S | 1 | E | m.p. 112-113 |
| 3a-59 | — | 4-Me | 3-F | S | H | S | 1 | E | m.p. 94-95 |
| 3a-60 | — | 4-Me | — | O | Me | S | 1 | E | m.p. 132-133 |

TABLE 14

TABLE 3-2

| Compound | $(R^1)_m$ | $(R^2)_p$ | $(R^3)_r$ | $Y^1$ | W | A | n | E/Z | Physical property |
|---|---|---|---|---|---|---|---|---|---|
| 3b-1 | — | — | — | S | H | S | 1 | Z | |
| 3b-2 | — | 4-Me | — | S | H | S | 1 | Z | |
| 3b-3 | — | 4-OMe | — | S | H | S | 1 | Z | |
| 3b-4 | — | 4-Cl | — | S | H | S | 1 | Z | |
| 3b-5 | — | 2,6-Cl$_2$ | — | S | H | S | 1 | Z | |
| 3b-6 | — | — | 4-Me | S | H | S | 1 | Z | |
| 3b-7 | — | — | 4-OMe | S | H | S | 1 | Z | |
| 3b-8 | — | — | 4-Cl | S | H | S | 1 | Z | |
| 3b-9 | — | — | 2,6-Cl$_2$ | S | H | S | 1 | Z | |
| 3b-10 | — | — | — | O | H | S | 1 | Z | |
| 3b-11 | — | 4-Me | — | O | H | S | 1 | Z | |

TABLE 14-continued

TABLE 3-2

| Compound | $(R^1)_m$ | $(R^2)_p$ | $(R^3)_r$ | $Y^1$ | W | A | n | E/Z | Physical property |
|---|---|---|---|---|---|---|---|---|---|
| 3b-12 | — | 4-OMe | — | O | H | S | 1 | Z | |
| 3b-13 | — | 4-Cl | — | O | H | S | 1 | Z | |
| 3b-14 | — | 2,6-Cl$_2$ | — | O | H | S | 1 | Z | |

TABLE 15

TABLE 3-2

| Compound | $(R^1)_m$ | $(R^2)_p$ | $(R^3)_r$ | $Y^1$ | W | A | n | E/Z | Physical property |
|---|---|---|---|---|---|---|---|---|---|
| 3c-1 | — | — | — | S | H | S | 2 | E | m.p. 106-107° C. |
| 3c-2 | — | 2-Me | — | S | H | S | 2 | E | |
| 3c-3 | — | 3-Me | — | S | H | S | 2 | E | |
| 3c-4 | — | 4-Me | — | S | H | S | 2 | E | |
| 3c-5 | — | 4-iPr | — | S | H | S | 2 | E | |
| 3c-6 | — | 4-OH | — | S | H | S | 2 | E | |
| 3c-7 | — | 4-OMe | — | S | H | S | 2 | E | |
| 3c-8 | — | 4-$NH_2$ | — | S | H | S | 2 | E | |
| 3c-9 | — | 4-$NMe_2$ | — | S | H | S | 2 | E | |
| 3c-10 | — | 4-F | — | S | H | S | 3 | E | |

TABLE 16

TABLE 3-3

| Compound | $(R^1)_m$ | $(R^2)_p$ | $(R^3)_r$ | $Y^1$ | W | A | n | E/Z | Physical property |
|---|---|---|---|---|---|---|---|---|---|
| 3c-11 | — | 4-Cl | — | S | H | S | 2 | E | m.p. 144-145 |
| 3c-12 | — | 2,6-$Cl_2$ | — | S | H | S | 2 | E | |
| 3c-13 | — | 4-$CF_3$ | — | S | H | S | 2 | E | |
| 3c-14 | — | 4-CN | — | S | H | S | 2 | E | |
| 3c-15 | — | 4-$NO_2$ | — | S | H | S | 2 | E | |
| 3c-16 | — | 4-Ph | — | S | H | S | 2 | E | |
| 3c-17 | — | 4-(Py-2-ly) | — | S | H | S | 2 | E | |
| 3c-18 | — | 4-$CO_2Me$ | — | S | H | S | 2 | E | |
| 3c-19 | — | 4-$SO_2Me$ | — | S | H | S | 2 | E | |
| 3c-20 | — | — | 4-Me | S | H | S | 2 | E | |
| 3c-21 | — | — | 4-OMe | S | H | S | 2 | E | |
| 3c-22 | — | — | 4-F | S | H | S | 3 | E | |
| 3c-23 | — | — | 4-Cl | S | H | S | 2 | E | |
| 3c-24 | — | — | 2,6-$Cl_2$ | S | H | S | 2 | E | |
| 3c-25 | 3-Me | 4-Me | — | S | H | S | 2 | E | |
| 3c-26 | 3-$Me_2$ | 4-Me | — | S | H | S | 2 | E | |
| 3c-27 | 1,1,2,2,3,3-$F_6$ | 4-Me | — | S | H | S | 2 | E | |
| 3c-28 | — | — | — | O | H | S | 2 | E | m.p. 95-96° C. |
| 3c-29 | — | 4-Me | — | O | H | S | 2 | E | |
| 3c-30 | — | 4-OMe | — | O | H | S | 2 | E | |
| 3c-31 | — | 4-Cl | — | O | H | S | 2 | E | |
| 3c-32 | — | 2,6-$Cl_2$ | — | O | H | S | 2 | E | |
| 3c-33 | — | — | 4-Me | O | H | S | 2 | E | |
| 3c-34 | — | — | 4-OMe | O | H | S | 2 | E | |
| 3c-35 | — | — | 4-Cl | O | H | S | 2 | E | |
| 3c-36 | — | — | 2,6-$Cl_2$ | O | H | S | 2 | E | |
| 3c-37 | — | — | — | O | H | S | 2 | E | |
| 3c-38 | — | 4-Me | — | O | H | S | 2 | E | m.p. 101-102° C. |
| 3c-39 | — | 4-OMe | — | O | H | S | 2 | E | m.p. 111-112° C. |
| 3c-40 | — | 4-Cl | — | O | H | S | 2 | E | |
| 3c-41 | — | 2,6-$Cl_2$ | — | O | H | S | 2 | E | |
| 3c-42 | — | — | 4-Me | O | H | S | 2 | E | |
| 3c-43 | — | — | 4-OMe | O | H | S | 2 | E | |
| 3c-44 | — | — | 4-Cl | O | H | S | 2 | E | |
| 3c-45 | — | — | 2,6-$Cl_2$ | O | H | S | 2 | E | |
| 3c-46 | — | — | — | S | Me | S | 2 | E | |
| 3c-47 | — | 4-Me | — | S | Me | S | 2 | E | |
| 3c-48 | — | 4-OMe | — | S | Me | S | 2 | E | |
| 3c-49 | — | 4-Cl | — | S | Me | S | 2 | E | |
| 3c-50 | — | 2,6-$Cl_2$ | — | S | Me | S | 2 | E | |

TABLE 17

TABLE 3-4

| Compound | $(R^1)_m$ | $(R^2)_p$ | $(R^3)_r$ | $Y^1$ | W | A | n | E/Z | Physical property |
|---|---|---|---|---|---|---|---|---|---|
| 3c-51 | — | — | — | S | $CF_3$ | S | 2 | E | |
| 3c-52 | — | 4-Me | — | S | $CF_3$ | S | 2 | E | |
| 3c-53 | — | 4-OMe | — | S | $CF_3$ | S | 2 | E | |
| 3c-54 | — | 4-Cl | — | S | $CF_3$ | S | 2 | E | |

TABLE 17-continued

TABLE 3-4

| Compound | $(R^1)_m$ | $(R^2)_p$ | $(R^3)_r$ | $Y^1$ | W | A | n | E/Z | Physical property |
|---|---|---|---|---|---|---|---|---|---|
| 3c-55 | — | 2,6-$Cl_2$ | — | S | $CF_3$ | S | 2 | E | |

TABLE 18

TABLE 3-4

| Compound | $(R^1)_m$ | $(R^2)_p$ | $(R^3)_r$ | $Y^1$ | W | A | n | E/Z | Physical property |
|---|---|---|---|---|---|---|---|---|---|
| 3c-56 | — | 3,4-$Me_2$ | — | S | H | S | 2 | E | m.p. 137-139 |
| 3c-57 | 3,3-$Me_2$ | 4-Me | — | O | H | S | 2 | E | m.p. 78-80 |
| 3c-58 | 2-Ph | 4-Me | — | O | H | S | 2 | E | Viscous oil |

TABLE 19

TABLE 3-4

| Compound | $(R^1)_m$ | $(R^2)_p$ | $(R^3)_r$ | $Y^1$ | W | A | n | E/Z | Physical property |
|---|---|---|---|---|---|---|---|---|---|
| 3d-1 | — | — | — | S | H | S | 2 | Z | |
| 3d-2 | — | 4-Me | — | S | H | S | 2 | Z | |
| 3d-3 | — | 4-OMe | — | S | H | S | 2 | Z | |
| 3d-4 | — | 4-Cl | — | S | H | S | 2 | Z | |
| 3d-5 | — | 2,6-$Cl_2$ | — | S | H | S | 2 | Z | |
| 3d-6 | — | — | 4-Me | S | H | S | 2 | Z | |
| 3d-7 | — | — | 4-OMe | S | H | S | 2 | Z | |
| 3d-8 | — | — | 4-Cl | S | H | S | 2 | Z | |
| 3d-9 | — | — | 2,8-$Cl_2$ | S | H | S | 2 | Z | |
| 3d-10 | — | — | — | O | H | S | 2 | Z | |
| 3d-11 | — | 4-Me | — | O | H | S | 2 | Z | |
| 3d-12 | — | 4-OMe | — | O | H | S | 2 | Z | |
| 3d-13 | — | 4-Cl | — | O | H | S | 2 | Z | |
| 3d-14 | — | 2,6-$Cl_2$ | — | O | H | S | 2 | Z | |

[Chemical formula 15]

-continued

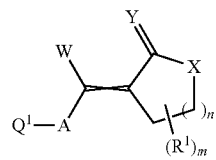

(IV)

TABLE 20

TABLE 4-1

| Compound | $(R^1)_m$ | $Q^1$ | X | Y | W | A | n | E/Z | Physical property |
|---|---|---|---|---|---|---|---|---|---|
| 4a-1 | — | Ph | S | N—CH=$CH_2$ | H | S | 1 | E | |
| 4a-2 | — | Ph | S | N—CH=CHPh | H | S | 1 | E | |
| 4a-3 | — | Ph | S | N—C≡CMe | H | S | 1 | E | |
| 4a-4 | — | Ph | S | N—cHex | H | S | 1 | E | |
| 4a-5 | — | Ph | S | N-Bn | H | S | 1 | E | |
| 4a-6 | — | Ph | S | N—NHPh | H | S | 1 | E | |
| 4a-7 | — | Ph | S | N—OPh | H | S | 1 | E | |
| 4a-8 | — | Ph | S | N—(Py-2-yl) | H | S | 1 | E | |
| 4a-9 | — | Ph | O | N—CH=$CH_2$ | H | S | 1 | E | |
| 4a-10 | — | Ph | O | N—CH=CHPh | H | S | 1 | E | |
| 4a-11 | — | Ph | O | N—C≡CMe | H | S | 1 | E | |
| 4a-12 | — | Ph | O | N—cHex | H | S | 1 | E | |
| 4a-13 | — | Ph | O | N-Bn | H | S | 1 | E | |
| 4a-14 | — | Ph | O | N—NHPh | H | S | 1 | E | |
| 4a-15 | — | Ph | O | N—OPh | H | S | 1 | E | |
| 4a-16 | — | Ph | O | N—(Py-2-yl) | H | S | 1 | E | |
| 4a-20 | — | Ph | N—cHex | S | H | S | 1 | E | |
| 4a-21 | — | Ph | N-Bn | S | H | S | 1 | E | |
| 4a-24 | — | Ph | N—(Py-2-yl) | S | H | S | 1 | E | |
| 4a-28 | — | Ph | N—cHex | O | H | S | 1 | E | |
| 4a-29 | — | Ph | N-Bn | O | H | S | 1 | E | |
| 4a-32 | — | Ph | N—(Py-2-yl) | O | H | S | 1 | E | m.p. 98-100 |

TABLE 20-continued

TABLE 4-1

| Compound | $(R^1)_m$ | $Q^1$ | X | Y | W | A | n | E/Z | Physical property |
|---|---|---|---|---|---|---|---|---|---|
| 4a-33 | — | CH=CH$_2$ | S | N—Ph | H | S | 1 | E | |
| 4a-34 | — | CH=CHPh | S | N—Ph | H | S | 1 | E | |
| 4a-35 | — | C≡CMe | S | N—Ph | H | S | 1 | E | |
| 4a-36 | — | cHex | S | N—Ph | H | S | 1 | E | |
| 4a-37 | — | Bn | S | N—Ph | H | S | 1 | E | |
| 4a-38 | — | Py-2-yl | S | N—Ph | H | S | 1 | E | |
| 4a-39 | — | CH=CH$_2$ | O | N—Ph | H | S | 1 | E | |
| 4a-40 | — | CH=CHPh | O | N—Ph | H | S | 1 | E | |
| 4a-41 | — | C≡CMe | O | N—Ph | H | S | 1 | E | |
| 4a-42 | — | cHex | O | N—Ph | H | S | 1 | E | |
| 4a-43 | — | Bn | O | N—Ph | H | S | 1 | E | |
| 4a-44 | — | Py-2-yl | O | N—Ph | H | S | 1 | E | |

TABLE 21

TABLE 4-1

| Compound | $(R^1)m$ | $Q^1$ | X | Y | W | A | n | E/Z | Physical property |
|---|---|---|---|---|---|---|---|---|---|
| 4a-45 | — | Pyrimidine-2-yl | O | N—Ph-4-Me | H | S | 1 | E | m.p. 156-157 |
| 4a-46 | — | Py-2-yl | O | N—Ph-4-Me | H | S | 1 | E | m.p. 122-123 |
| 4a-47 | — | Cyclopentyl | O | N—Ph-4-Me | H | S | 1 | E | m.p. 63-64 |
| 4a-48 | — | Bn | S | N—Ph-4-Me | H | S | 1 | E | Viscous oil |

TABLE 22

TABLE 4-1

| Compound | $(R^1)_m$ | $Q^1$ | X | Y | W | A | n | E/Z | Physical property |
|---|---|---|---|---|---|---|---|---|---|
| 4a-49 | — | cHex | N—Ph | S | H | S | 1 | E | |
| 4a-50 | — | Bn | N—Ph | S | H | S | 1 | E | |
| 4a-51 | — | Py-2-yl | N—Ph | S | H | S | 1 | E | |
| 4a-52 | — | cHex | N—Ph | O | H | S | 1 | E | |
| 4a-53 | — | Bn | N—Ph | O | H | S | 1 | E | |
| 4a-54 | — | Py-2-yl | N—Ph | O | H | S | 1 | E | |

TABLE 23

TABLE 4-1

| Compound | $(R^1)m$ | $Q^1$ | X | Y | W | A | n | E/Z | Physical property |
|---|---|---|---|---|---|---|---|---|---|
| 4a-55 | — | Cyclopentyl | N—Ph-4-Me | O | H | S | 1 | E | nD22.4-1.6143 |
| 4a-56 | — | Py-2-yl | N—Ph-4-Me | O | H | S | 1 | E | m.p. 114-115 |

TABLE 24

TABLE 4-2

| Compound | $(R^1)_m$ | $Q^1$ | X | Y | W | A | n | E/Z | Physical property |
|---|---|---|---|---|---|---|---|---|---|
| 4b-1 | — | Ph | S | N—CH=CH$_2$ | H | S | 2 | E | |
| 4b-2 | — | Ph | S | N—CH=CHPh | H | S | 2 | E | |
| 4b-3 | — | Ph | S | N—C≡CMe | H | S | 2 | E | |
| 4b-4 | — | Ph | S | N—cHex | H | S | 2 | E | |
| 4b-5 | — | Ph | S | N-Bn | H | S | 2 | E | |

TABLE 24-continued

TABLE 4-2

| Compound | $(R^1)_m$ | $Q^1$ | X | Y | W | A | n | E/Z | Physical property |
|---|---|---|---|---|---|---|---|---|---|
| 4b-6 | — | Ph | S | N—NHPh | H | S | 2 | E | |
| 4b-7 | — | Ph | S | N—OPh | H | S | 2 | E | |
| 4b-8 | — | Ph | S | N—(Py-2-yl) | H | S | 2 | E | |
| 4b-9 | — | Ph | O | N—CH=CH₂ | H | S | 2 | E | |
| 4b-10 | — | Ph | O | N—CH=CHPh | H | S | 2 | E | |
| 4b-11 | — | Ph | O | N—C≡CMe | H | S | 2 | E | |
| 4b-12 | — | Ph | O | N—cHex | H | S | 2 | E | |
| 4b-13 | — | Ph | O | N-Bn | H | S | 2 | E | |
| 4b-14 | — | Ph | O | N—NHPh | H | S | 2 | E | |
| 4b-15 | — | Ph | O | N—OPh | H | S | 2 | E | |
| 4b-16 | — | Ph | O | N—(Py-2-yl) | H | S | 2 | E | |
| 4b-17 | — | Ph | N—cHex | S | H | S | 2 | E | |
| 4b-18 | — | Ph | N-Bn | S | H | S | 2 | E | |
| 4b-19 | — | Ph | N—(Py-2-yl) | S | H | S | 2 | E | |
| 4b-20 | — | Ph | N—cHex | O | H | S | 2 | E | |
| 4b-21 | — | Ph | N-Bn | O | H | S | 2 | E | |
| 4b-22 | — | Ph | N—(Py-2-yl) | O | H | S | 2 | E | |
| 4b-23 | — | CH=CH₂ | S | N—Ph | H | S | 2 | E | |
| 4b-24 | — | CH=CHPh | S | N—Ph | H | S | 2 | E | |
| 4b-25 | — | C≡CMe | S | N—Ph | H | S | 2 | E | |
| 4b-26 | — | cHex | S | N—Ph | H | S | 2 | E | |
| 4b-27 | — | Bn | S | N—Ph | H | S | 2 | E | |
| 4b-28 | — | Py-2-yl | S | N—Ph | H | S | 2 | E | |
| 4b-29 | — | CH=CH₂ | O | N—Ph | H | S | 2 | E | |
| 4b-30 | — | CH=CHPh | O | N—Ph | H | S | 2 | E | |
| 4b-31 | — | C≡CMe | O | N—Ph | H | S | 2 | E | |
| 4b-32 | — | cHex | O | N—Ph | H | S | 2 | E | |
| 4b-33 | — | Bn | O | N—Ph | H | S | 2 | E | |
| 4b-34 | — | Py-2-yl | O | N—Ph | H | S | 2 | E | |
| 4b-35 | — | cHex | N—Ph | S | H | S | 2 | E | |
| 4b-36 | — | Bn | N—Ph | S | H | S | 2 | E | |
| 4b-37 | — | Py-2-yl | N—Ph | S | H | S | 2 | E | |
| 4b-38 | — | cHex | N—Ph | O | H | S | 2 | E | |
| 4b-39 | — | Bn | N—Ph | O | H | S | 2 | E | |
| 4b-40 | — | Py-2-yl | N—Ph | O | H | S | 2 | E | |

TABLE 25

TABLE 4-2

| Compound | $(R^1)m$ | $Q^1$ | X | Y | W | A | n | E/Z | Physical property |
|---|---|---|---|---|---|---|---|---|---|
| 4b-41 | — | Ph | N—Me | O | H | S | 2 | E | nD22.4-1.6170 |

TABLE 26

TABLE 4-3

| Compound | $(R^1)_m$ | $Q^1$ | X | Y | W | A | n | E/Z | Physical property |
|---|---|---|---|---|---|---|---|---|---|
| 4c-1 | — | Ph | S | N—CH=CH₂ | H | S | 1 | Z | |
| 4c-2 | — | Ph | S | N—CH=CHPh | H | S | 1 | Z | |
| 4c-3 | — | Ph | S | N—C≡CMe | H | S | 1 | Z | |
| 4c-4 | — | Ph | S | N—cHex | H | S | 1 | Z | |
| 4c-5 | — | Ph | S | N-Bn | H | S | 1 | Z | |
| 4c-6 | — | Ph | S | N—NHPh | H | S | 1 | Z | |
| 4c-7 | — | Ph | S | N—OPh | H | S | 1 | Z | |
| 4c-8 | — | Ph | S | N—(Py-2-yl) | H | S | 1 | Z | |
| 4c-9 | — | Ph | O | N—CH=CH₂ | H | S | 1 | Z | |
| 4c-10 | — | Ph | O | N—CH=CHPh | H | S | 1 | Z | |
| 4c-11 | — | Ph | O | N—C≡CMe | H | S | 1 | Z | |
| 4c-12 | — | Ph | O | N—cHex | H | S | 1 | Z | |

TABLE 26-continued

TABLE 4-3

| Compound | $(R^1)_m$ | $Q^1$ | X | Y | W | A | n | E/Z | Physical property |
|---|---|---|---|---|---|---|---|---|---|
| 4c-13 | — | Ph | O | N-Bn | H | S | 1 | Z | |
| 4c-14 | — | Ph | O | N—NHPh | H | S | 1 | Z | |
| 4o-15 | — | Ph | O | N—OPh | H | S | 1 | Z | |
| 4c-16 | — | Ph | O | N—(Py-2-yl) | H | S | 1 | Z | |
| 4c-17 | — | Ph | N—cHex | S | H | S | 1 | Z | |
| 4c-18 | — | Ph | N-Bn | S | H | S | 1 | Z | |
| 4c-19 | — | Ph | N—(Py-2-yl) | S | H | S | 1 | Z | |
| 4c-20 | — | Ph | N—cHex | O | H | S | 1 | Z | |
| 4c-21 | — | Ph | N-Bn | O | H | S | 1 | Z | |
| 4c-22 | — | Ph | N—(Py-2-yl) | O | H | S | 1 | Z | |
| 4c-23 | — | CH=CH$_2$ | S | N—Ph | H | S | 1 | Z | |
| 4c-24 | — | CH=CHPh | S | N—Ph | H | S | 1 | Z | |
| 4c-25 | — | C≡CMe | S | N—Ph | H | S | 1 | Z | |
| 4c-26 | — | cHex | S | N—Ph | H | S | 1 | Z | |
| 4c-27 | — | Bn | S | N—Ph | H | S | 1 | Z | |
| 4c-28 | — | Py-2-yl | S | N—Ph | H | S | 1 | Z | |
| 4c-29 | — | CH=CH$_2$ | O | N—Ph | H | S | 1 | Z | |
| 4c-30 | — | CH=CHPh | O | N—Ph | H | S | 1 | Z | |
| 4c-31 | — | C≡CMe | O | N—Ph | H | S | 1 | Z | |
| 4c-32 | — | cHex | O | N—Ph | H | S | 1 | Z | |
| 4c-33 | — | Bn | O | N—Ph | H | S | 1 | Z | |
| 4c-34 | — | Py-2-yl | O | N—Ph | H | S | 1 | Z | |
| 4c-35 | — | cHex | N—Ph | S | H | S | 1 | Z | |
| 4c-36 | — | Bn | N—Ph | S | H | S | 1 | Z | |
| 4c-37 | — | Py-2-yl | N—Ph | S | H | S | 1 | Z | |
| 4c-38 | — | cHex | N—Ph | O | H | S | 1 | Z | |
| 4c-39 | — | Bn | N—Ph | O | H | S | 1 | Z | |
| 4c-40 | — | Py-2-yl | N—Ph | O | H | S | 1 | Z | |

TABLE 27

TABLE 4-4

| Compound | $(R^1)_m$ | $Q^1$ | X | Y | W | A | n | E/Z | Physical property |
|---|---|---|---|---|---|---|---|---|---|
| 4d-1 | — | Ph | S | N—CH=CH$_2$ | H | S | 2 | Z | |
| 4d-2 | — | Ph | S | N—CH=CHPh | H | S | 2 | Z | |
| 4d-3 | — | Ph | S | N—C≡CMe | H | S | 2 | Z | |
| 4d-4 | — | Ph | S | N—cHex | H | S | 2 | Z | |
| 4d-5 | — | Ph | S | N-Bn | H | S | 2 | Z | |
| 4d-6 | — | Ph | S | N—NHPh | H | S | 2 | Z | |
| 4d-7 | — | Ph | S | N—OPh | H | S | 2 | Z | |
| 4d-8 | — | Ph | S | N—(Py-2-yl) | H | S | 2 | Z | |
| 4d-9 | — | Ph | O | N—CH=CH$_2$ | H | S | 2 | Z | |
| 4d-10 | — | Ph | O | N—CH=CHPh | H | S | 2 | Z | |
| 4d-11 | — | Ph | O | N—C≡CMe | H | S | 2 | Z | |
| 4d-12 | — | Ph | O | N—cHex | H | S | 2 | Z | |
| 4d-13 | — | Ph | O | N-Bn | H | S | 2 | Z | |
| 4d-14 | — | Ph | O | N—NHPh | H | S | 2 | Z | |
| 4d-15 | — | Ph | O | N—OPh | H | S | 2 | Z | |
| 4d-16 | — | Ph | O | N—(Py-2-yl) | H | S | 2 | Z | |
| 4d-17 | — | Ph | N—cHex | S | H | S | 2 | Z | |
| 4d-18 | — | Ph | N-Bn | S | H | S | 2 | Z | |
| 4d-19 | — | Ph | N—(Py-2-yl) | S | H | S | 2 | Z | |
| 4d-20 | — | Ph | N—cHex | O | H | S | 2 | Z | |
| 4d-21 | — | Ph | N-Bn | O | H | S | 2 | Z | |
| 4d-22 | — | Ph | N—(Py-2-yl) | O | H | S | 2 | Z | |
| 4d-23 | — | CH=CH$_2$ | S | N—Ph | H | S | 2 | Z | |
| 4d-24 | — | CH=CHPh | S | N—Ph | H | S | 2 | Z | |
| 4d-25 | — | C≡CMe | S | N—Ph | H | S | 2 | Z | |
| 4d-26 | — | cHex | S | N—Ph | H | S | 2 | Z | |
| 4d-27 | — | Bn | S | N—Ph | H | S | 2 | Z | |
| 4d-28 | — | Py-2-yl | S | N—Ph | H | S | 2 | Z | |
| 4d-29 | — | CH=CH$_2$ | O | N—Ph | H | S | 2 | Z | |
| 4d-30 | — | CH=CHPh | O | N—Ph | H | S | 2 | Z | |
| 4d-31 | — | C≡CMe | O | N—Ph | H | S | 2 | Z | |
| 4d-32 | — | cHex | O | N—Ph | H | S | 2 | Z | |

TABLE 27-continued

TABLE 4-4

| Compound | $(R^1)_m$ | $Q^1$ | X | Y | W | A | n | E/Z | Physical property |
|---|---|---|---|---|---|---|---|---|---|
| 4d-33 | — | Bn | O | N—Ph | H | S | 2 | Z | |
| 4d-34 | — | Py-2-yl | O | N—Ph | H | S | 2 | Z | |
| 4d-35 | — | cHex | N—Ph | S | H | S | 2 | Z | |
| 4d-36 | — | Bn | N—Ph | S | H | S | 2 | Z | |
| 4d-37 | — | Py-2-yl | N—Ph | S | H | S | 2 | Z | |
| 4d-38 | — | cHex | N—Ph | O | H | S | 2 | Z | |
| 4d-39 | — | Bn | N—Ph | O | H | S | 2 | Z | |
| 4d-40 | — | Py-2-yl | N—Ph | O | H | S | 2 | Z | |
| 4e-1 | — | Ph | S | N-(4-MePh) | H | S | 3 | Z | nD22.9-1.6037 |
| 4e-2 | — | Ph | S | N-(4-MePh) | H | S | 3 | Z | |
| 4e-3 | — | Ph | N-(4-MePh) | S | H | S | 3 | Z | |
| 4e-4 | — | Ph | N-(4-MePh) | S | H | S | 3 | Z | |

TABLE 28

TABLE 5-1

| Compound | Structural formula | Physical property |
|---|---|---|
| 5a-1 | | Viscous oil |
| 5a-2 | | m.p. 113-114 |
| 5a-3 | | m.p. 111-112° C. |
| 5a-4 | | Viscous oil |
| 5a-5 | | Viscous oil |
| 5a-6 | | Viscous oil |

TABLE 28-continued

TABLE 5-1

| Compound | Structural formula | Physical property |
|---|---|---|
| 5a-7 | | |
| 5b-1 | | m.p. 113-114 |

¹H-NMR analyses of some produced compounds described in the above tables are shown below.

Compound (1a-1): 2.99 (dt, 2.0 Hz, 6.8 Hz, 2H), 3.21 (t, 6.8 Hz, 2H)), 7.0 (d, 2H), 7.1 (t, 1H), 7.25-7.4 (m, 5H), 7.48-7.55 (m, 3H)

Compound (1a-4): 2.33 (s, 3H), 2.99 (dt, 2.0 Hz, 6.8 Hz, 2H), 3.22 (t, 6.8 Hz, 2H), 6.91 (d, 8.3 Hz, 2H), 7.14 (d, 8.6 Hz, 2H), 7.29-7.38 (m, 3H), 7.48-7.54 (m, 3H)

Compound (1a-3): 2.34 (s, 3H), 2.99 (dt, 2.0 Hz, 6.8 Hz, 2H), 3.23 (t, 6.8 Hz, 2H), 6.79-6.82 (m, 3H), 6.92 (d, 1H), 7.20-7.40 (m, 3H), 7.48-7.51 (m, 2H), 7.54 (t, 2.0 Hz, 1H)

Compound (1a-34): 2.89 (dt, 2.9 Hz, 7.4 Hz, 2H), 4.42 (t, 7.4 Hz, 2H), 7.05-7.20 (m, 3H), 7.25-7.45 (m, 5H), 7.47-7.60 (m, 3H)

Compound (2a-1): 2.15 (m, 2H), 2.68 (dt, 2.0 Hz, 6.8 Hz, 2H), 2.92 (t, 6.8 Hz, 2H), 6.8-7.6 (m, 11H)

Compound (2a-32): 1.99 (m, 2H), 2.59 (dt, 2.4 Hz, 6.8 Hz, 2H), 4.14 (t, 5.1 Hz, 2H), 6.99-7.52 (m, 10H), 7.79 (t, 2.4 Hz, 1H)

Compound (2a-4): 2.14 (m, 2H), 2.32 (s, 3H), 2.69 (dt, 2.0 Hz, 6.8 Hz, 2H), 2.90 (t, 6.8 Hz, 2H), 6.7-7.6 (m, 11H)

Compound (1a-5): 1.24 (d, 6H), 2.89 (m, 1H), 2.99 (dt, 2.0 Hz, 6.8 Hz, 2H), 3.22 (t, 6.8 Hz, 2H), 6.94 (d, 8.3 Hz, 2H), 7.1-7.6 (m, 8H)

Compound (1a-33): 1.44 (d, 8.0 Hz, 3H), 2.33 (s, 3H), 2.57 (ddd, 2.3 Hz, 6.8 Hz, 15.8 Hz, 1H), 3.14 (ddd, 2.1 Hz, 6.8 Hz, 15.8 Hz, 1H), 3.76 (m, 1H), 6.89 (d, 8.3 Hz, 2H), 7.14 (d, 8.9 Hz, 2H), 7.27-7.55 (m, 6H)

Compound (1a-2): 2.16 (s, 3H), 3.02 (dt, 2.0 Hz, 6.5 Hz, 2H), 3.23 (t, 6.5 Hz, 2H), 6.83-7.58 (m, 10H)

Compound (1a-31): 2.33 (s, 3H), 2.35 (s, 3H), 2.97 (dt, 2.0 Hz, 6.8 Hz, 2H), 3.21 (t, 6.8 Hz, 2H), 6.90 (d, 8.0 Hz, 2H), 7.15 (m, 4H), 7.38 (d, 8.0 Hz, 2H), 7.48 (t, 2.0 Hz, 1H)

Compound (1a-32): 2.33 (s, 3H), 2.97 (dt, 2.0 Hz, 6.5 Hz, 2H), 3.22 (t, 6.5 Hz, 2H), 6.89 (d, 6.2 Hz, 2H), 7.02-7.15 (m, 4H), 7.41-7.52 (m, 3H)

Compound (4e-1): 1.96 (m, 4H), 2.32 (s, 3H), 2.62 (m, 2H), 2.85 (m, 2H), 6.76-7.6 (m, 10H)

Compound (3a-2): 2.27 (s, 3H), 3.02 (dt, 2.7 Hz, 7.4 Hz, 2H), 3.99 (t, 7.4 Hz, 3H), 7.16-7.53 (m, 9H), 7.88 (t, 2.7 Hz, 1H)

Compound (1a-71): 2.33 (s, 3H), 2.36 (t, 3H), 3.06-3.24 (m, 4H), 6.85 (d, 2H), 7.15 (d, 2H), 7.3-7.5 (m, 5H)

Compound (1a-83): 2.29 (s, 3H), 2.40 (t, 3H), 3.00 (dt, 2H), 4.31 (t, 2H), 6.99 (d, 2H), 7.09 (d, 8.0 Hz, 2H), 7.3-7.5 (m, 5H)

Compound (1a-84): 0.8-1.8 (m, 7H), 2.31 (s, 3H), 2.6 (m, 1H), 2.98 (m, 1H), 4.55 (m, 1H), 6.7-7.6 (m, 10H)

Compound (1a-85): 2.29 (s, 1H), 2.80 (ddd, 1H), 3.32 (ddd, 1H), 5.57 (t, 1H), 7.07 (d, 2H), 7.17 (d, 2H), 7.2-7.6 (m, 11H)

Compound (1a-86): 1.45 (s, 6H), 2.30 (s, 3H), 2.66 (d, 2H), 7.1 (m, 4H), 7.3-7.4 (m, 3H), 7.45-7.53 (m, 3H)

Compound (1b-36): 1.87 (s, 3H), 2.34 (s, 3H), 3.01 (t, 2H), 3.14 (t, 2H), 6.85 (d, 2H), 7.00 (d, 2H), 7.3-7.6 (m, 5H)

Compound (2a-34): 2.01-2.14 (m, 2H), 2.64-2.76 (m, 2H), 3.79 (s, 3H), 4.37-0.53 (m, 2H), 6.85 (d, 2H), 7.31-7.49 (m, 8H)

Compound (2a-78): 2.14 (m, 2H), 2.32 (s, 3H), 2.66 (dt, 2H), 2.89 (m, 2H), 6.75 (d, 2H), 7.0-7.15 (m, 4H), 7.37 (t, 1H), 7.48 (m, 2H)

Compound (2a-79): 2.01 (m, 2H), 2.58 (dt, 2H), 4.14 (m, 2H), 6.95 (d, 2H), 7.2-7.5 (m, 5H), 7.51 (d, 2H), 7.78 (brs, 1H)

Compound (2a-80): 2.16 (m, 2H), 2.68 (dt, 2H), 2.92 (t, 2H), 6.8 (d, 2H), 7.25-7.51 (m, 8H)

Compound (2a-82): 1.98 (m, 2H), 2.20 (s, 6H), 2.58 (dt, 2H), 4.14 (t, 2H), 6.79 (m, 2H), 7.00 (d, 2H), 7.3-7.52 (m, 5H), 7.73 (t, 1H)

Compound (2a-85): 1.33 (s, 6H), 1.88 (t, 2H), 2.29 (s, 3H), 2.58 (d t, 2H), 6.9-7.5 (m, 9H), 7.79 (t, 1H)

Compound (2a-86): 2.0-2.3 (m, 2H), 2.27 (s, 3H), 2.67 (m, 2H), 5.18 (dd, 1H), 7.0-7.55 (m, 14H), 7.81 (br, 1H)

Compound (2b-36): 2.08 (m, 2H), 2.34 (s, 3H), 2.66 (dt, 2H), 2.94 (m, 2H). 6.53 (t, 1H), 6.8-7.49 (m, 8H)

Compound (3a-60): 2.01 (s, 3H), 2.33 (s, 3H), 3.20 (t, 2H), 3.79 (t, 2H), 7.15 (d, 2H), 7.3-7.5 (m, 7H)

Compound (3c-56): 2.14 (m, 2H), 2.27 (s, 6H), 2.67 (dt, 2H), 3.74 (t, 2H), 6.9-7.0 (m, 2H), 7.2-7.5 (m, 6H), 8.53 (t, 1.8 Hz)

Compound (3c-58): 2.28-2.41 (m, 5H), 2.5-2.9 (m, 2H), 4.98 (t, 1H), 7.1-7.7 (m, 15H)

Compound (5a-1): 1.2-2.1 (m, 9H), 2.29-2.42 (m, 1H), 2.66 (ddd, 3H), 4.30 (m, 1H), 7.04 (m, 5H), 7.25-7.4 (m, 3H), 7.49 (dd, 2H), 7.76 (br, 1H)

Compound (5a-4): 1.31-1.40 (m, 2H), 1.46-1.56 (m, 2H), 1.71-1.82 (m, 4H), 2.32 (s, 3H), 2.98 (m, 1H), 4.51 (m, 1H), 6.68 (s, 1H), 7.09-7.54 (m, 9H)

Compound (5a-5): 1.75-1.80 (m, 2H), 2.14-2.17 (m, 2H), 2.29 (q, 1H), 2.26-2.33 (m, 1H), 3.25 (q, 1H), 3.87 (brs, 1H), 5.56-5.61 (m, 1H), 5.89-5.92 (m, 1H), 6.84 (d, 2H), 7.25-7.39 (m, 6H), 7.49 (d, 2H)

Compound (5a-6): 2.35 (s, 3H), 7.13-7.36 (m, 7H), 7.40-7.46 (m, 4H), 7.62 (d, 2H), 7.71 (s, 1H)

Formulation Examples

Next, some formulation examples of compositions of the present invention are shown, but additives and addition ratios are not limited to these formulation examples, and can be modified over a wide range. Moreover, the term "parts" used in these formulation examples indicate "mass parts."

Formulation Example 1

Wettable Powder

| | |
|---|---|
| Compound of the present invention | 40 parts |
| Diatom earth | 53 parts |
| Fatty alcohol sulfate | 4 parts |
| Alkylnaphtalene sulfonate | 3 parts |

The foregoing is uniformly mixed and finely pulverized to obtain a wettable powder of 40% active ingredient.

Formulation Example 2

Emulsion

| | |
|---|---|
| Compound of the present invention | 30 parts |
| Xylene | 33 parts |
| Dimethylform amid | 30 parts |
| Polyoxyethylene alkylallyl ether | 7 parts |

The foregoing is mixed and dissolved to obtain an emulsion of 30% active ingredient.

Formulation Example 3

Dust Agent

| | |
|---|---|
| Compound of the present invention | 10 parts |
| Talc | 89 parts |
| Polyoxyethylene alkyl aryl ether | 1 part |

The foregoing is uniformly mixed and finely pulverized to obtain a dust agent of 10% active ingredient.

Formulation Example 4

Granular Agent

| | |
|---|---|
| Compound of the present invention | 5 parts |
| Clay | 73 parts |
| Bentonite | 20 parts |
| Sodium dioctylsulfosuccinate salt | 1 part |
| Sodium phosphate | 1 part |

The foregoing is thoroughly pulverized and mixed, water is added, and kneading is thoroughly conducted, after which granulation and drying are conducted to obtain a granular agent of 5% active ingredient.

Formulation Example 5

Suspension

| | |
|---|---|
| Compound of the present invention | 10 parts |
| Sodium lignin sulfonate | 4 parts |
| Sodium dodecylbenzene sulfonate | 1 parts |
| Xanthan gum | 0.2 parts |
| Water | 84.8 parts |

The foregoing is mixed, and wet crushing is conducted until particle size is 1 microns or less to obtain a suspension of a 10% active ingredient.

Test examples of the harmful organism control agents obtained in the foregoing manner are shown below.

Test Example 1

Confirmation of Efficacy Against *Pseudaletia separate*

A chemical solution was prepared according to the prescription of the emulsion shown in the aforementioned Formulation Example 2 and diluted with water to a compound concentration of 125 ppm. Maize leaves were soaked in the resulting chemical solution for 30 seconds and air-dried. Then the leaves were put on Petri dishes lined with a filter paper, followed by inoculating 5 second-instar larvae. The Petri dishes were covered with a glass cover and placed in a temperature-controlled room of which the temperature was 25° C. and the humidity was 65%. Mortality was investigated after five days, and the insect mortality rate was obtained. The test was repeated twice.

The test was carried out with compounds 1a-1, 1a-2, 1a-3, 1a-4, 1a-31, 1a-32, 1a-33, 1a-35, 1a-80, 1a-82, 1a-84, 1a-85, 1a-86, 2a-1, 2a-4, 2a-7, 2a-78, 2a-79, 2a-80, 2a-81, 2a-83, 2a-84, 2a-85, 2a-86, 2a-87, 2b-36, 3a-27, 3c-58, 4a-45, 4e-1, 5a-1, 5a-2, 5a-3 and 5a-5 to confirm the efficacy against *Pseudaletia separate*, and as a result, all of the compounds exhibited a 100% mortality rate.

Test Example 2

Confirmation of Efficacy Against *Aphis gossypii*

Cucumber seedlings, 10 days after germination, which are seeded in a pot with a diameter of 9 cm were inoculated with adult *Aphis gossypii*. After one day, the adult insects were removed, and the cucumber seedlings which were parasitized with the produced offspring were subjected to application of a chemical solution that was prepared according to the prescription of the emulsion shown in the aforementioned Formulation Example 2. The chemical solution was diluted with water to a compound concentration of 125 ppm. The cucumber seedlings were placed in a temperature-controlled room of which the temperature was 25° C. and the humidity was 65%. Mortality was investigated after five days, and the insect mortality rate was obtained.

The test was repeated twice.

57

The test was carried out with compounds 1a-2, 1a-3, 1a-4, 1a-31, 1a-32, 1a-33, 1a-80, 1a-84, 1a-85, 1a-86, 2a-1, 2a-4, 2a-7, 2a-78, 2a-79, 2a-80, 2a-81, 2a-82, 2a-84, 2b-36, 3a-27, 4e-1, 5a-1 and 5a-5 to confirm the efficacy against *Aphis gossypii*, and as a result, all of the compounds exhibited a 100% mortality rate.

Test Example 3

Confirmation of Efficacy Against *Bemisia tabaci*

A chemical solution was prepared according to the prescription of the emulsion shown in the aforementioned Formulation Example 2 and diluted with water to a compound concentration of 125 ppm. Detached tomato leaves were sprayed with the resulting chemical solution and air-dried. Then, the leaves were set on flasks in a manner that the surface of the leaves face upward. 7 pairs of B type adult *Bemisia tabaci* were inoculated into the flasks, and the flasks were placed in a temperature-controlled room of which the temperature was 25° C. and the humidity was 65%. The insect mortality rate was investigated after three days. The test was repeated twice.

The test was carried out with compounds 1a-1, 1a-2, 1a-3, 1a-4, 1a-5, 1a-31, 1a-32, 1a-33, 1a-35, 1a-80, 1a-82, 1a-84, 1a-85, 1a-86, 2a-1, 2a-4, 2a-7, 2a-78, 2a-79, 2a-80, 2a-81, 2a-82, 2a-83, 2a-84, 2a-85, 2a-86, 2a-87, 3a-1, 3a-27, 4e-1, 5a-1, 5a-3 and 5a-5 to confirm the efficacy against *Bemisia tabaci*, and as a result, all of the compounds exhibited a 100% mortality rate.

Test Example 4

Confirmation of Efficacy Against *Tetranychus urticae*

Bean seedlings, 7-10 days after generation, which are seeded in a pot with a diameter of 9 cm were inoculated with 17 female adults of *Tetranychus urticae* with organophosphate resistance on their first leaves. Then, a chemical solution was prepared according to the prescription of the emulsion shown in the aforementioned Formulation Example 2 and diluted with water to a compound concentration of 125 ppm. The resulting chemical solution was sprayed on the bean seedlings. Then, the bean seedlings were place in a temperature-controlled room of which the temperature was 25° C. and the humidity was 65%. The insect mortality rate was investigated after three days. The test was repeated twice.

The test was carried out with compounds 2a-78, 2a-83, 2a-84, 2a-85, 2a-86 and 5a-5 to confirm the efficacy against *Tetranychus urticae*, and as a result, all of the compounds exhibited a 100% mortality rate.

INDUSTRIAL APPLICABILITY

According to the present invention, a 1-heterodiene derivative having a new structure and salt thereof can be provided. In addition, a harmful organism control agent containing, as an active ingredient, the 1-heterodiene derivative or salt thereof can be provided. The harmful organism control agent has an excellent biological activity, especially a biological activity against insects or mites, and has a high safety.

The invention claimed is:
1. A 1-heterodiene derivative represented by formula (1) or salt thereof:

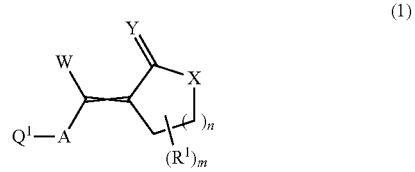

wherein $Q^1$ represents an optionally substituted C2-6 alkenyl group, an optionally substituted C2-6 alkynyl group, an optionally substituted C3-6 cycloalkyl group, an optionally substituted C4-8 cycloalkenyl group, an optionally substituted C6-10 aryl group, an optionally substituted benzyl group or an optionally substituted heterocyclic group, W represents hydrogen atom or an optionally substituted C1-6 alkyl group, X represents oxygen atom, sulfur atom or N-$Q^2$ ($Q^2$ represents an optionally substituted C2-6 alkenyl group, an optionally substituted C2-6 alkynyl group, an optionally substituted C3-6 cycloalkyl group, an optionally substituted C4-8 cycloalkenyl group, an optionally substituted C6-10 aryl group, an optionally substituted benzyl group, an optionally substituted C6-10 aryloxy group, an optionally substituted C6-10 arylamino group or an optionally substituted heterocyclic group), Y represents oxygen atom, sulfur atom or N-$Q^3$ ($Q^3$ represents an optionally substituted C2-6 alkenyl group, an optionally substituted C2-6 alkynyl group, an optionally substituted C3-6 cycloalkyl group, an optionally substituted C4-8 cycloalkenyl group, an optionally substituted C6-10 aryl group, an optionally substituted benzyl group, an optionally substituted C6-10 aryloxy group, an optionally substituted C6-10 arylamino group or an optionally substituted heterocyclic group), provided that when X represents oxygen atom or sulfur atom, Y represents N-$Q^3$, when X represents N-$Q^2$, Y represents oxygen atom or sulfur atom, A represents oxygen atom, sulfur atom, sulfonyl group or sulfinyl group, n represents an integer of 1 to 4, $R^1$ represents an optionally substituted C1-6 alkyl group, an optionally substituted C2-6 alkenyl group, an optionally substituted C2-6 alkynyl group, an optionally substituted C3-6 cycloalkyl group, an optionally substituted C4-8 cycloalkenyl group, an optionally substituted C6-10 aryl group, an optionally substituted heterocyclic group, an optionally substituted C1-11 acyl group, an optionally substituted (1-imino) C1-6 alkyl group, an optionally substituted hydroxy group, an optionally substituted amino group, an optionally substituted mercapto group, a substituted sulfonyl group, a substituted sulfinyl group, a silyl group, a halogen group, cyano group or nitro group, m represents an integer of 0 to 10, when m is 2 or more, $R^1$ may be the same or different from each other, more than one $R^1$ may bond together to form an optionally substituted 3- to 8-membered ring, the 1-heterodiene derivative exists in E-form, Z-form or a mixture thereof according to the carbon-carbon undefined double stereo bond in formula (1).

2. A 1-heterodiene derivative represented by formula (2) or salt thereof:

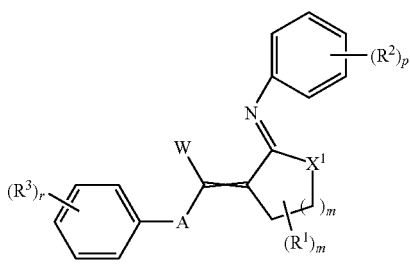

(2)

wherein W, A, R¹, m and n are as defined above,
X¹ represents oxygen atom or sulfur atom,
R² represent an optionally substituted C1-6 alkyl group, an optionally substituted C2-6 alkenyl group, an optionally substituted C2-6 alkynyl group, an optionally substituted C3-6 cycloalkyl group, an optionally substituted C4-8 cycloalkenyl group, an optionally substituted C6-10 aryl group, an optionally substituted heterocyclic group, an optionally substituted C1-11 acyl group, an optionally substituted (1-imino) C1-6 alkyl group, an optionally substituted hydroxy group, an optionally substituted amino group, an optionally substituted mercapto group, a substituted sulfonyl group, a substituted sulfinyl group, a silyl group, a halogen group, cyano group or nitro group,
p represents an integer of 0 to 5, when p is 2 or more, R² may be the same or different from each other, more than one R² may bond together to form an optionally substituted 3- to 8-membered ring,
R³ represents an optionally substituted C1-6 alkyl group, an optionally substituted C2-6 alkenyl group, an optionally substituted C2-6 alkynyl group, an optionally substituted C3-6 cycloalkyl group, an optionally substituted C4-8 cycloalkenyl group, an optionally substituted C6-10 aryl group, an optionally substituted heterocyclic group, an optionally substituted C1-11 acyl group, an optionally substituted (1-imino) C1-6 alkyl group, an optionally substituted hydroxy group, an optionally substituted amino group, an optionally substituted mercapto group, a substituted sulfonyl group, a substituted sulfinyl group, a silyl group, a halogeno group, cyano group or nitro group,
r represents an integer of 0 to 5, when r is 2 or more, R³ may be the same or different from each other, more than one R³ may bond together to form an optionally substituted 3- to 8-membered ring,
the 1-heterodiene derivative exists in E-form, Z-form or a mixture thereof according to the carbon-carbon undefined double stereo bond of formula (2).

* * * * *